US009101544B2

(12) United States Patent
Grenier et al.

(10) Patent No.: US 9,101,544 B2
(45) Date of Patent: Aug. 11, 2015

(54) CONTROLLED RELEASE NISOLDIPINE COMPOSITIONS

(75) Inventors: Pascal Grenier, Kappelen (FR); Alain Nhamias, Bartenheim (FR); Guy Vergnault, Kembes (FR)

(73) Assignee: Jagotec AG, Muttenz (CH)

( * ) Notice: Subject to any disclaimer, the term of this patent is extended or adjusted under 35 U.S.C. 154(b) by 521 days.

(21) Appl. No.: 11/846,896

(22) Filed: Aug. 29, 2007

(65) Prior Publication Data

US 2008/0063711 A1 Mar. 13, 2008

Related U.S. Application Data

(60) Provisional application No. 60/824,043, filed on Aug. 30, 2006, provisional application No. 60/824,054, filed on Aug. 30, 2006.

(51) Int. Cl.
*A61K 9/28* (2006.01)
*A61K 9/20* (2006.01)

(52) U.S. Cl.
CPC ............. *A61K 9/2866* (2013.01); *A61K 9/2086* (2013.01); *A61K 9/2846* (2013.01)

(58) Field of Classification Search
CPC .. A61K 9/2086; A61K 9/2846; A61K 9/2866
See application file for complete search history.

(56) References Cited

U.S. PATENT DOCUMENTS

| 4,892,741 | A |   | 1/1990  | Ohm et al. |
| 4,933,186 | A |   | 6/1990  | Ohm et al. |
| 4,966,772 | A |   | 10/1990 | Ohm et al. |
| 4,968,508 | A | * | 11/1990 | Oren et al. ............ 424/468 |

(Continued)

FOREIGN PATENT DOCUMENTS

| EP | 0526862 A1 | 2/1993 |
| EP | 1681051 A1 | 7/2006 |

(Continued)

OTHER PUBLICATIONS

Conte and Maggi, "A flexible technology for the linear, pulsatile and delayed release of drugs, allowing for easy accommodation of difficult in vitro targets", *J. Control Release*, 64(1-3):263-8 (2000).

(Continued)

*Primary Examiner* — Aradhana Sasan
(74) *Attorney, Agent, or Firm* — Mintz, Levin, Cohn, Ferris, Glovsky and Popeo PC; Muriel Liberto, Esq.

(57) ABSTRACT

Controlled release oral dosage formulations containing calcium channel blockers, and methods of use thereof, are provided for the once-a-day treatment of cardiovascular disorders, such as hypertension, angina, and cardiac arrhythmia. The active agent is preferably a dihydropyridine calcium channel blocker, such as nisoldipine. The formulation provides an increase in the bioavailability of the calcium channel blocker as compared to the bioavailability of the calcium channel blocker in other drug delivery formulations known in the art. In one embodiment, the formulation provides an increase in the bioavailability of the calcium channel blocker, nisoldipine, as compared to the same dose of nisoldipine in the coat-core version of the drug (SULAR®). The formulation can be in the form of a trilayer tablet containing a core or central layer and one or more barrier layers.

24 Claims, 3 Drawing Sheets

(56) References Cited

U.S. PATENT DOCUMENTS

| | | | |
|---|---|---|---|
| 5,015,479 | A | 5/1991 | Mulligan et al. |
| 5,071,642 | A | 12/1991 | Lahr et al. |
| 5,209,933 | A | 5/1993 | MacFarlane et al. |
| 5,422,123 | A | 6/1995 | Conte et al. |
| 5,439,687 | A * | 8/1995 | Compassi ............ 424/468 |
| 5,626,874 | A | 5/1997 | Conte et al. |
| 5,667,804 | A | 9/1997 | Wong et al. |
| 5,736,159 | A | 4/1998 | Chen et al. |
| 5,783,212 | A | 7/1998 | Fassihi et al. |
| 5,900,425 | A | 5/1999 | Kanikanti et al. |
| 5,922,352 | A * | 7/1999 | Chen et al. ............ 424/465 |
| 5,955,096 | A | 9/1999 | Santos et al. |
| 6,020,000 | A | 2/2000 | Wong et al. |
| 6,027,748 | A | 2/2000 | Conte et al. |
| 6,083,532 | A * | 7/2000 | Zhang et al. ............ 424/468 |
| 6,096,339 | A | 8/2000 | Ayer et al. |
| 6,103,263 | A | 8/2000 | Lee et al. |
| 6,221,395 | B1 | 4/2001 | Maggi et al. |
| 6,235,313 | B1 | 5/2001 | Mathiowitz et al. |
| 6,294,200 | B1 | 9/2001 | Conte et al. |
| 6,387,404 | B2 | 5/2002 | Oshlack et al. |
| 6,866,866 | B1 | 3/2005 | Chen et al. |
| 6,923,988 | B2 | 8/2005 | Patel et al. |
| 6,962,717 | B1 | 11/2005 | Huber et al. |
| 2004/0198789 | A1 | 10/2004 | Leonardi et al. |
| 2008/0057123 | A1 | 3/2008 | Grenier et al. |

FOREIGN PATENT DOCUMENTS

| | | |
|---|---|---|
| WO | WO-0048577 A1 | 8/2000 |
| WO | WO 01/78688 | 10/2001 |
| WO | WO 2004/084870 | 10/2004 |
| WO | WO 2005/070463 | 8/2005 |
| WO | WO 2006/035416 | 4/2006 |
| WO | WO 2006/035417 | 4/2006 |
| WO | WO-2008025532 A1 | 3/2008 |

OTHER PUBLICATIONS

Hernandez, at al., "Influence of route of administration and dosage form in the pharmacokinetics and bioavailability of salbutamol", *Eur. J. Drug Metab. Pharmacokinet.*, 22(2):145-50 (1997).

Acarturk, "Formulation and investigation of nicardipine HC1-alginate gel beads with factorial design-based studies", *Eur. J. Pharm. Sci.*, 6:241-246 (1998).

Heinig, et al., "Pharmacokinetics of the controlled-release nisoldipine coat-core tablet formulation", *International Journal of Clinical Pharmacology and Therapeutics*, 35(8):341-351 (1997).

Plosker, et al. "Nisoldipine coat-core. A review of its pharmacology and therapeutic efficacy in hypertension," *Drugs* 52(2):232-53(1996).

Defina, et al. "Nifedipine gastrointestinal therapeutic system versus nifedipine coat-core: comparison of efficacy via 24-hour ambulatory blood pressure monitoring," *Ann. Pharmacother*. 31(7-8): 819-822 (1997).

Wang, et al. "Validated LC-MS-MS method for determination of m-nisoldipine polymorphs in rat plasma and its application to pharmacokinetic studies," *J Chromatogr. B Analyt. Techno.I Biomed. Life Sci.* 835(1-2):71-6 (2006).

Chowdary et al., "Controlled release of nifedipine from mucoadhesive tablets of its inclusion complexes with b-cyclodextrin", *Pharmazie*, 58(10):721-724 (2003).

Drugs & Therapy Perspectives, "For Rational Drug Use and Disease Management", vol. 9, No. 1 (1997).

Fernandes et al., "Physiochemical characterization and in vitro dissolution behavior of nicardipine-cyclodextrins inclusion compounds", *Eur. J. Pharm. Sci.*, 15:79-88 (2002).

Langtry et al., "Nisoldipine coat-core—A Review of its Pharmacodynamic and Pharmacokinetic Properties and Clinical Efficacy in the Management of Ischemic Heart Disease", *Drugs*, 53(5):867-884 (1997).

Moursy et al., "Formulation and evaluation of sustained release floating capsules of nicardipine hydrochloride", *Pharmazie*, 58:38-43 (2003).

Ofoefule et al., "Effect of Polyethyleneglycol 4000 (PEG4000) Solution on the in Vitro Release Profile of Nifedipine from Polymer Matrices", *Biol. Pharm. Bull.*, 20(5):574-576 (1997).

Petersen et al., "In vitro Release of Felodipine from Original Brand and Generic Products", *Drug Res.*, 53(1):40-43 (2003).

Tanaka et al., "Development of novel sustained-release system, disintegration-controlled matrix tablet (DCMT) with solid dispersion granules of nilvadipine", *J. Contr. Rel.*, 108:386-395 (2005).

Yang et al., "Formulation of nisoldipine sustained release tablets", *Chin. J. New Drugs*, 10:905-906 (2004).

"Eudragit®: Acrylic Polymers for Solid Oral Dosage Forms." *Evonik Industries*. Web. Jul. 11, 2013. http://eudragit.evonik.com/product/eudragit/Documents/evonik-brochure-eudragit-product.pdf.

\* cited by examiner

CONTROLLED RELEASE NISOLDIPINE COMPOSITIONS

CROSS-REFERENCE TO RELATED APPLICATIONS

This application claims priority to U.S. Provisional Application No. 60/824,043, filed on Aug. 30, 2006 and U.S. Provisional Application No. 60/824,054, filed on Aug. 30, 2006.

FIELD OF THE INVENTION

The present invention relates to controlled release formulations containing a calcium channel blocker and methods of use thereof. More particularly, the method and compositions relate to an oral dosage form containing nisoldipine as a once-a-day treatment for hypertension and other cardiovascular disorders.

BACKGROUND OF THE INVENTION

Calcium channel blockers are a heterogeneous group of drugs that prevent or slow the entry of calcium into cells by regulating cellular calcium channels. (Remington, The Science and Practice of pharmacy, Nineteenth Edition, Mack Publishing Company, Eaton, Pa., p. 963 (1995)). The regulation of calcium entry into the cells of the cardiovascular system is of paramount importance to the proper functioning of this system. Cardiac and vascular smooth muscle cells have calcium channels located within the cell membrane. Calcium influx through these channels initiates a process of electromechanical coupling which ultimately leads to muscle contraction. The ability to regulate the entry of calcium into cardiac and vascular smooth muscle cells is a powerful therapeutic approach in the treatment of angina and hypertension. Likewise, blocking calcium influx into cardiac tissues and conduction systems can provide a useful approach for controlling certain types of arrhythmia.

The dihydropyridine calcium channel blocker, nisoldipine, is a yellow crystalline substance, which is practically insoluble in water, but soluble in ethanol. Nisoldipine coat-core (marketed as SULAR® by Sciele Pharma, Inc.) is a long-acting formulation of the drug, suitable for once daily administration in the treatment of patients with hypertension. SULAR® is an FDA approved controlled-release formulation of the calcium channel blocker, nisoldipine, which employs coat-core technology, and has been marketed for the treatment of hypertension since 1995. SULAR® tablets consist of an external coating and an internal core. Both the coating and the core contain nisoldipine; the coating as a slow release formulation and the core as an immediate or fast release formulation. In clinical trials in patients with mild to moderate hypertension, SULAR® has shown efficacy and tolerability similar to that of other calcium antagonists, and antihypertensive efficacy equivalent to that of agents from various other drug classes including beta-blockers, thiazide diuretics and ACE inhibitors. SULAR® demonstrates dose proportional pharmacokinetics and has a plasma half-life of about 7-12 hours with a mean $T_{max}$ of about 6-12 hours. The absolute bioavailability of nisoldipine from SULAR® is about 5%.

Unlike beta-blockers and thiazide diuretics, calcium antagonists (including nisoldipine coat-core) are not associated with clinically significant adverse metabolic effects on the serum lipid profile or glycaemic control. Nisoldipine coat-core maintains consistent plasma drug concentrations and antihypertensive effects throughout the 24-hour dosage interval, thereby attenuating intermittent reflex increases in sympathetic activity. In addition, the high degree of vasoselectivity of nisoldipine minimizes negative inotropic effects which may be observed with less selective agents such as nifedipine (Plosker, D L and Faulds, D. *Drugs,* 52(2), 232-53 (1996)).

Although the coat-core technology has been shown to be safe for the delivery of calcium channel blockers, studies have shown that there are slightly more adverse effects with the coat-core systems compared to other drug delivery systems, especially with respect to the drug, nifedipine (Defina et al. Ann Pharmacother. 31 (7-8): 819-822 (1997)). The coat-core technology also requires the use of specialized equipment which can be costly.

There exists a need for controlled release formulations that provides a lower dose of the drug, which may decrease the cost of manufacturing and may eliminate or diminish unwanted side effects, and which can be manufactured using conventional equipment.

Therefore, it is an object of the invention to provide controlled release formulations and methods of making and using thereof that provide alternative pharmacokinetic release profiles that may eliminate or diminish unwanted side effects and which are easier and cheaper to manufacture.

It is further an object of the invention to provide a controlled release formulation of a calcium channel blocker, such as nisoldipine, which is effective in the treatment of cardiovascular disorders, especially, hypertension, and which provides advantages over known formulations such as SULAR®.

It is further an object of the invention to provide a controlled release formulation of a calcium channel blocker, where the amount of the drug is efficacious, yet reduced, as compared to known formulations such as SULAR®.

It is yet another object of the invention to provide a controlled release formulation of a calcium channel blocker, where the bioavailability of the drug is increased compared to the bioavailability of the drug to known formulations such as SULAR®.

BRIEF SUMMARY OF THE INVENTION

Controlled release oral dosage formulations containing calcium channel blockers, and methods of use thereof, are provided for the once-a-day treatment of cardiovascular disorders, such as hypertension, angina, and cardiac arrhythmia. The active agent is preferably a dihydropyridine calcium channel blocker, such as nisoldipine, nifedipine, nicardipine, nimodipine, amlodipine, felodipine, isradipine, lacidipine, lercanidipine, and pharmaceutically acceptable salts thereof. In a preferred embodiment, the dihydropyridine calcium channel blocker is nisoldipine, or analogues, derivatives, or polymorphs thereof. The formulation can be administered in any solid oral dosage form such as a tablet or caplet.

In one embodiment, the controlled release formulation is a tablet containing a core or central layer containing a dihydropyridine calcium channel blocker, such as nisoldipine, and at least one barrier layer above or below the central layer which contains one or more erodible, swellable and/or gellable polymeric materials. The concentration of the one or more polymers is from about 5% to about 90% by weight of the barrier layer, preferably from about 25% to about 75% by weight of the barrier. In a preferred embodiment, the tablet is a trilayer tablet which contains a core or central layer, and two barrier layers, one above the central layer and one below. The barrier layers may be the same or different in composition and thickness. The core and/or barrier layers may contain one or more pharmaceutically acceptable additives, excipients, or carriers.

The core or central layer may contain one or more polymeric materials that modulate (i.e. slow and/or accelerate) the release of the calcium channel blocker. The concentration of the polymeric material is from about 1% to about 90% by weight by weight of the core, preferably from about 10% to about 45% by weight of the core.

The central layer and/or the barrier layers may also contain one or more adjuvants, which, in combination with the polymeric materials, further modulate release of the calcium channel blocker. The concentration of the adjuvant(s) is from about 1% to about 25% by weight of the compositions, preferably from about 5% to about 15% by weight of the composition.

The formulation may be coated with one or more modified release coatings, which further modulate the release of the active agent from the core or central layer. Suitable coatings include taste mask coatings, enteric coatings, sustained or extended release coatings, and delayed release coatings. The dosage forms may also be coated for aesthetic reasons such as to impart a color to the dosage form or to apply a surface finish to the dosage form.

The formulation provides an increase in the bioavailability of the calcium channel blocker as compared to the bioavailability of the calcium channel blocker in other drug delivery formulations known in the art. In a preferred embodiment, the formulation provides an increase in the bioavailability of the calcium channel blocker, nisoldipine, as compared to the same dose of nisoldipine in the coat-core version of the drug (SULAR®).

In one embodiment, the composition contains one or more controlled release elements in an amount effective to provide a controlled release of the calcium channel blocker. In one embodiment, the composition provides a $T_{max}$ of the calcium channel blocker from about 3.85 to about 15 hours and an $AUC_{last}$ (i.e., the AUC measured at 72 hours after administration) of the calcium channel blocker from about 38 hr*ng/ml to about 87 hr*ng/ml under fasting conditions based on a 40 mg dose. In another embodiment, the composition provides a $T_{max}$ of the calcium channel blocker from about 3.85 to about 15 hours and a $C_{max}$ of the calcium channel blocker from about 1.5 to about 6.5 ng/mL under fasting conditions based on a 40 mg dose.

The controlled release formulations described herein may contain a reduced dose of the calcium channel blocker, but a similar pharmacokinetic profile when compared to other calcium channel blocker formulations known and used in the art. In a preferred embodiment, the controlled release formulation contains a reduced dose of nisoldipine, but a similar pharmacokinetic profile, when compared to SULAR®.

One embodiment, a trilayer tablet containing 40 mg nisoldipine (Formulation A) exhibited a roughly 16% increase in the $AUC_{last}$ compared to SULAR® 40 mg. This suggests that the dose of nisoldipine in the trilayer tablet can be reduced by approximately 16% (i.e. to 34 mg) and still provide an effective amount of the drug. Accordingly, the 10 mg, 20 mg, 30 mg, and 40 mg dosage strengths of SULAR can be replaced with reduced, bioequivalent dosage strengths (for example, 8.5 mg, 17 mg, 25.5 mg, and 34 mg) of the compositions defined herein. This may result in lower manufacturing costs due to the lower doses required to obtain the desired therapeutic effect.

DETAILED DESCRIPTION OF THE INVENTION

I. Definitions

Figure 1:
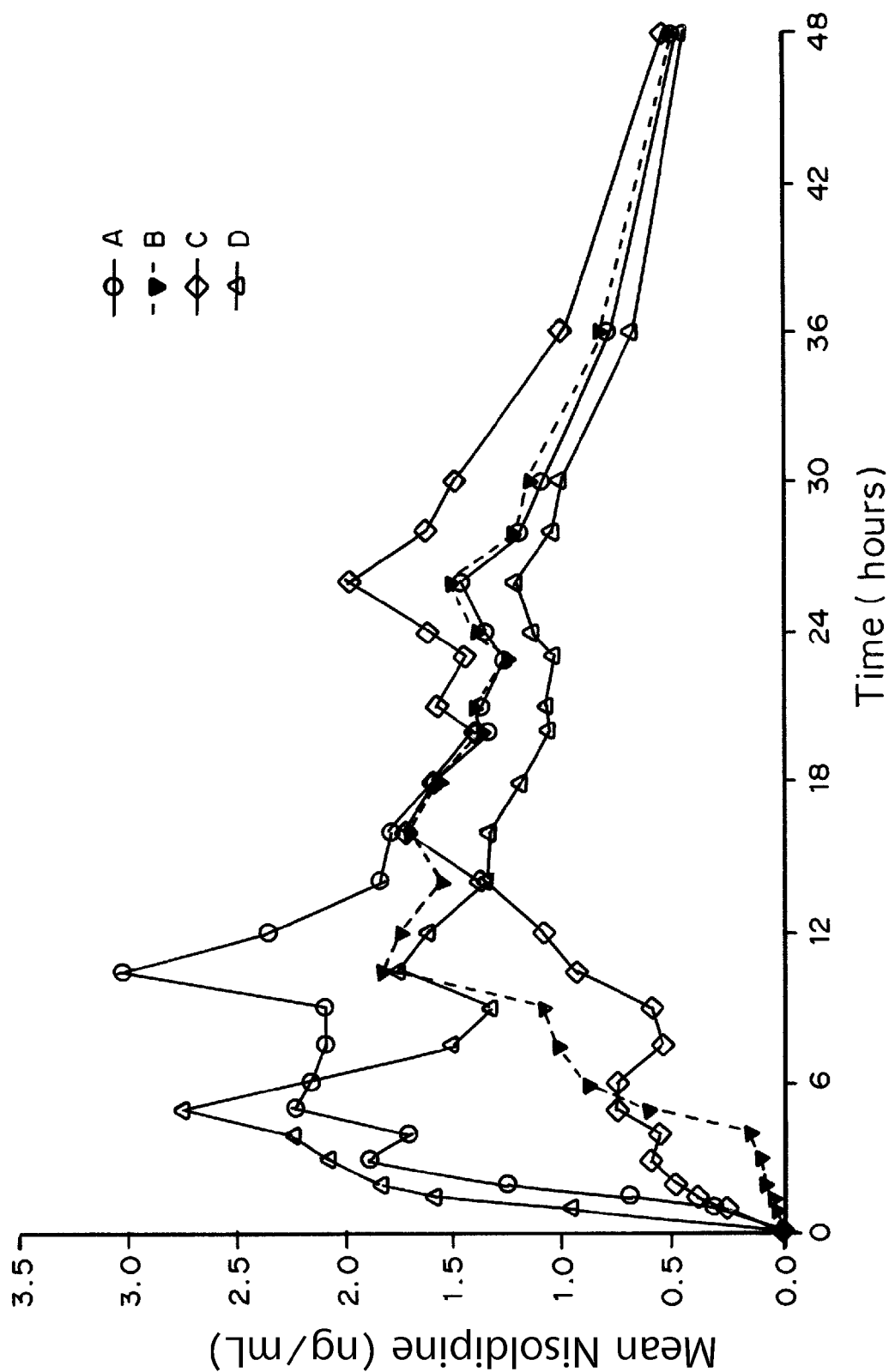
FIG. 1 is a graph of the mean nisoldipine concentration versus time (in hours) for three test formulations (treatments A, B, and C) and the reference product SULAR® (treatment D) under fasting conditions.

"Taste masking coating", as used herein, refers to a pH dependent coating that is insoluble in the mouth but dissolves in the acidic pH of the stomach.

"Extended release coating", as used herein, refers to a pH independent substance that will act as a barrier to control the diffusion of the drug from its core complex into the gastrointestinal fluids.

"Enteric coating", as used herein, refers to a coating material which remains substantially intact in the acid environment of the stomach, but which dissolves in the neutral environment of the intestines.

"Delayed release coating", as used herein, refers to a pH dependent coating that is insoluble in the acidic pH of the stomach and the pH within the mid to the upper small intestine, but dissolves within the lower small intestine or upper large intestine.

"$C_{max}$", as used herein, refers to the peak concentration in blood plasma. Unless otherwise stated, $C_{max}$ refers to the peak concentration of the calcium channel blocker in blood plasma.

"$T_{max}$", as used herein, refers to the time to peak concentration in blood plasma. Unless otherwise stated, $T_{max}$ refers to the time to peak concentration of the calcium channel blocker in blood plasma.

"$\lambda_z$", as used herein, refers to the elimination rate constant.

"$T_{1/2}$", as used herein, refers to the terminal half-life.

"$AUC_{last}$" as used herein refers to the area under the concentration-time curve from time-zero to the time of the last quantifiable concentration. Unless indicated otherwise, the $AUC_{last}$ reported herein represents the AUC measured at 72 hours post-dose.

"$AUC_{inf}$", as used herein, refers to the area under the plasma concentration time curve from time-zero extrapolated to infinity.

"Bioavailability", as used herein, refers to the rate and extent of uptake of the active ingredient or active agent from a drug product.

"Bioequivalence", as used herein, refers to the equivalent release of the same drug substance from two or more drug products or formulations. This leads to an equivalent rate and extent of absorption from these formulations.

As used herein, an "analog" of a chemical compound is a compound that, by way of example, resembles another in structure but is not necessarily an isomer (e.g., 5-fluorouracil is an analog of thymine).

As used herein, a "derivative" of a compound refers to a chemical compound that may be produced from another compound of similar structure in one or more steps. Derivatives generally involve the addition and/or modification of one or more functional groups on the parent compound.

As used herein, "controlled release elements" refers to materials that modulate release of the active agent from the formulation. The controlled release elements may be located in the core and/or the barrier layer(s). The controlled release elements may be organic or inorganic, naturally occurring or synthetic, materials including, but not limited to, polymeric materials, triglycerides, derivatives of triglycerides, fatty acids and salts of fatty acids, talc, small organic molecules and salts thereof, talc, boric acid, and colloidal silica.

As used herein, "coat-core nisoldipine 40 mg tablet" for purposes of comparison of pharmacokinetics and dosage refers to the version of the drug marketed as SULAR®, containing 8 mg of nisoldipine in the core and 32 mg of nisoldipine in the coat.

II. Compositions

Controlled release formulations containing calcium channel blockers, and methods of use thereof, are described for the once-a-day treatment of cardiovascular disorders, such as hypertension, angina, and cardiac arrhythmia. In one embodiment, the formulation is a multilayer tablet containing a core or central layer containing a dihydropyridine calcium channel blocker and at least one barrier layer above and/or below the central layer which contains one or more erodible, swellable and/or gellable polymeric materials. Similar formulations have been described in U.S. Pat. Nos. 5,626,874; 5,422,123; and 6,027,748 to Conte et al.

A. Core or Central Layer

1. Calcium Channel Blocker

The core or central layer of the tablet contains a calcium channel blocker. In one embodiment, the calcium channel blocker is a dihydropyridine calcium channel blocker. Suitable dihydropyridine calcium channel blockers include, but are not limited to, nisoldipine, nifedipine, nicardipine, nimodipine, amlodipine, felodipine, isradipine, lacidipine, lercanidipine, and pharmaceutically acceptable salts thereof. In a preferred embodiment, the calcium channel blocker is nisoldipine or a derivative, analogue, or polymorph thereof. Derivatives of nisoldipine, such as m-nisoldipine, are described in Wang et al., *J. Chrom. B*, 835, 71-76 (2006)). The concentration of the calcium channel blocker is generally from about 0.1% to about 90% by weight of the tablet, preferably from about 0.5% to about 20% by weight of the tablet, more preferably from about 1% to about 10% by weight of the tablet. Alternatively, the concentration of the calcium channel blocker is generally from about 0.1% to about 90% by weight of the core, preferably from about 0.5% to about 20% of the core, more preferably from about 1% to about 10% of the core.

The calcium channel blockers can be chiral or achiral. Chiral molecules can exist as a single enantiomer, a mixture of enantiomers or diastereomers or a racemic mixture. As used herein, the term "stereoisomers" refers to compounds made up of the same atoms having the same bond order but having different three-dimensional arrangements of atoms which are not interchangeable. The three-dimensional structures are called configurations. As used herein, the term "enantiomers" refers to two stereoisomers which are non-superimposable mirror images of one another. As used herein, the term "optical isomer" is equivalent to the term "enantiomer". As used herein the term "diastereomer" refers to two stereoisomers which are not mirror images and are not superimposable. The terms "racemate", "racemic mixture" or "racemic modification" refer to a mixture of equal parts of enantiomers. The term "chiral center" refers to a carbon atom to which four different groups are attached. Choice of the appropriate chiral column, eluent, and conditions necessary to effect separation of the pair of enantiomers is well known to one of ordinary skill in the art using standard techniques (see e.g. Jacques, J. et al., "Enantiomers, Racemates, and Resolutions", John Wiley and Sons, Inc. 1981).

As used herein, "pharmaceutically acceptable salts" refer to derivatives of the compounds listed above, wherein the parent compound is modified by making the acid or base addition salt thereof. Example of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, naphthalenesulfonic, methanesulfonic, ethane disulfonic, oxalic, and isethionic salts.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like diethyl ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704; and "Handbook of Pharmaceutical Salts; Properties, Selection, and Use," P. Heinrich Stahl and Camille G. Wermuth, Eds., Wiley-VCH, Weinheim, 2002.

As generally used herein "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

2. Controlled Release Elements

The core or central layer may also contain an enteric material to delay the release of the one or more active agents until the formulation reaches the absorption window. Suitable enteric materials include, but are not limited to, cellulose acetate phthalate, alginates, alkali-soluble acrylic resins, hydroxypropyl methylcellulose phthalate, methacrylate-methacrylic acid co-polymers, polyvinyl acetate phthalate, styrol maleic acid copolymers, and the like, and combinations thereof. In one embodiment, the enteric material is cellulose acetate phthalate. The concentration of the enteric material is from about 0.1% to about 20% by weight, preferably about 1 to 15%, more preferably about 5 to 10% by weight of the composition.

In addition to the calcium channel blocker, the core or central layer of the tablet may also contain one or more polymeric materials that modulate (i.e. slow and/or accelerate) the release of the calcium channel blocker. Suitable polymeric materials include, but are not limited to, crosslinked polyvinylpyrrolidone, hydroxypropylmethylcellulose, hydroxypropylcellulose, crosslinked sodium carboxymethylcellulose, carboxymethyl starch, starch and derivatives thereof, acrylic and methacrylic acid polymers and copolymers, polyesters, polyanhydrides, polymethylvinylether/anhydride copolymers, potassium methacrylate-divinylbenzene copolymers, polyvinylalcohols, glucan, scleroglucan, mannan, betacyclodextrins and cyclodextrin derivatives containing linear and/or branched polymeric chains. In one embodiment, the core or central layer contains hydroxypropylmethylcellulose. The concentration of the polymeric materials is from about 1% to about 90% by weight of the core, preferably from about 10% to about 45% by weight of the core.

These polymers are available commercially, and are characterized by different chemico-physical characteristics such as solubility and gel formation. For example, the erodibility, gelation, and ability to swell of hydroxypropylmethyl cellulose can vary based on the molecular weight of the polymer and the degree of substitution. Therefore, one skilled in the art would be able to select from among polymers with the same molecular structure but differing in the molecular weight and/or viscosity, based on the desired release profile of the active agent. In one embodiment, the core or central layer contains Methocel® K4M, a hydroxypropyl methycellulose having a methoxy content of 19-24%, a hydroxypropoxyl content of 7-12%, and an apparent viscosity, as measured by rotation, of 2308-3755 mPa (Colorcon, West Point, Pa.). In another embodiment, the core or central layer contains Methocel® K100LV, a hydroxypropyl methycellulose having a methoxy content of 19-24%, a hydroxypropoxyl content of 7-12%, and an apparent viscosity, as measured by rotation, of 78-117 mPa (Colorcon, West Point, Pa.)

3. Other Active Agents

The calcium channel blocker may be combined with one or more additional active agents. Suitable active agents include, but are not limited to, other anti-hypertensive drugs such as ACE inhibitors, angiotensin receptor inhibitors, beta-blockers, and other calcium channel blockers.

B. Barrier Layer(s)

The barrier layer(s) serve to prevent, for a predetermined amount of time, the release of the drug contained in the central layer or core. The tablet can contain one or more barrier layers. When two barrier layers are present, the barriers layers may have the same composition or different compositions and/or the same thickness or different thicknesses.

In one embodiment, the barrier layer(s) contain(s) one or more swellable, erodible and/or gellable polymers. In one embodiment, the swellable, erodible, and/or gellable polymer is hydroxypropylmethyl-cellulose, The weight average molecular weight of the hydroxypropyl-methylcellulose is from about 1000 to about 4,000,000, more preferably from about 2000 to about 2,000,000. In one embodiment, the barrier layer(s) contain Methocel® E5, a hydroxypropyl methycellulose having a methoxy content of 28-30%, a hydroxypropoxyl content of 7-12%, and an apparent viscosity, as measured by rotation, of 4.2-6.1 mPa (Colorcon, West Point, Pa.). In another embodiment, the barrier layer(s) contain Methocel® E50, a hydroxypropyl methycellulose having a methoxy content of 28-30%, a hydroxypropoxyl content of 7-12%, and an apparent viscosity, as measured by rotation, of 39-59 mPa (Colorcon, West Point, Pa.). In still another embodiment, one barrier layer contains Methocel® E5 and the second barrier layer contains Methocel® E50.

Other suitable polymers include, but are not limited to, carboxyvinyl polymers; polyvinylalcohols; glucans, scleroglucans; mannans; xanthans; alginic acid and its derivatives; polyanhydrides; polyaminoacids; methylvinylethers/maleic anhydride copolymers; carboxymethylcellulose and its derivatives; ethylcellulose; methylcellulose; and other cellulosic polymers.

The polymers are present in an amount from about 5% to about 90% by weight of the barrier layer, preferably from about 25% to about 75% by weight of the barrier layer.

C. Other Release-Modifying Agents

The core layer and/or the barrier layer(s) may also contain one or more adjuvants, which in combination with the polymeric materials allow for further modulation of the release of the active agent based on the desired release profile of the active agent. Suitable adjuvants include, but are not limited to, glyceryl monostearate, triglyceride derivatives, semi-synthetic glycerides, hydrogenated castor oil, glyceryl palmitostearate, cetyl alcohol, polyvinylpyrrolidone, glycerol, ethylcellulose, methylcellulose, sodium carboxymethylcellulose, other natural or synthetic substances well known to those skilled in the art, and combinations thereof. Other suitable adjuvants include, but are not limited to, magnesium stearate, stearic acid, talc, sodium benzoate, boric acid, polyoxyethylenglycols and colloidal silica. The concentration of the adjuvant(s) is from about 1% to about 25% by weight of the compositions, preferably from about 5% to about 15% by weight of the composition.

D. Additives, Excipients and Carriers

Formulations may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to, plasticizers, diluents, binders, lubricants, surfactants, pH modifying agents, anti-adherents, disintegrators, fillers, pigments, colorants, stabilizing agents, flavoring agents, glidants, and combinations thereof.

Suitable plasticizers include, but are not limited to, hydrogenated castor oil, cetyl alcohol, cetostearyl alcohol, fatty acids, glycerides and triglycerides and derivatives thereof, and polyoxyethylenglycols and derivatives thereof.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. The amount of active substance released in the first administration phase may be programmed BY regulating the exposed surface and the components constituting the layer (a) matrix, based on solubility.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets may also contain minor amounts of nontoxic auxiliary substances such as wetting or emulsifying agents, dyes, pH buffering agents, or preservatives.

E. Modified Release Coatings

Compositions described herein, in the form of a solid dosage form, may be coated with one or more modified release coatings, which further modulate the release of the active agent from the core or central layer. Suitable coatings include, but are not limited to, coatings which are soluble in, or permeable to, the acidic medium of the stomach (i.e. taste mask coatings and immediate release coatings); coatings which are insoluble in the acidic medium of the stomach but are soluble in the neutral environment of the small intestine (i.e. enteric coatings); coatings which are insoluble in the stomach and the environment of the mid to the upper small intestine, but dissolve in the lower small intestine or upper large intestine (i.e. delayed release coatings); and combinations thereof. The dosage forms may also be coated for aesthetic reasons such as to impart a color to the dosage form or to apply a surface finish to the dosage form.

1. Immediate Release Coatings

Immediate release coatings are formed of a polymer that dissolves within the oral cavity upon contact with saliva or which are insoluble in the neutral pH of the oral cavity and which dissolve at the low pH of the stomach.

Coatings which dissolve in the mouth may have properties such as mucoadhesion, to prolong contact of the particles with the buccal, sublingual or other oral cavity surfaces to enhance uptake of the drug. Many mucoadhesive polymers are known and typically are characterized by a high density of carboxylic groups. See for example, U.S. Pat. Nos. 6,235,313 and 5,955,096 to Mathiowitz et al.

Coatings which dissolve in the stomach are typically used to provide properties such as taste-masking. The cationic polymer Eudragit® E 100 (Rohm Pharma) carries amino groups. Its films are, therefore, insoluble in the neutral medium of saliva, but dissolve by salt formation in the acid environment of the stomach. Such film coatings with a thickness of approximately 10 micrometers can prevent medication with a bitter or unpleasant taste from dissolving in the mouth upon ingestion or during swallowing. The protective film dissolves quickly under the acidic conditions in the stomach allowing for the active ingredient to be released. The coating composition may include conventional additives, such as plasticizers, pigments, colorants, stabilizing agents, glidants, etc.

2. Sustained or Extended Release Coatings

Sustained or extended release of the drug is possible with the use of a diffusion barrier coating on the drug-resin complex particles. Suitable coating materials include, but are not limited to, copolymers available under the trade name Eudragit® (Rohm Pharma), such as poly(ethylacrylate-methylmethacrylate-triethylammonioethyl-metharylate chloride) (Eudragit® RS and Eudragit® RL) and poly(ethylacrylate-methylmethacrylate) (Eudragit® NE). Aqueous dispersions of such polymers are available under the trade names Eudragit® RS 30 D, Eudragit® RL 30 D and Eudragit® NE 30 D.

These copolymers may be used alone, in admixture with each other, and in admixture with plasticizers (for example, triethyl citrate), pigments, and other substances to alter the characteristics of the coating. In general, the major components of the coating should be insoluble in, and permeable to, water. However, it may be desirable to incorporate a water-soluble substance, such as methyl cellulose, to alter the permeability of the coating.

The coating materials may be applied as a suspension in an aqueous fluid. The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers are, but not limited to, polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent may be used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

3. Enteric Coatings

Enteric coated dosage forms can be prepared as described in references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et. al., (Media, Pa.: Williams and Wilkins, 1995). Examples of suitable coating materials include but are not limited to cellulose polymers, such as cellulose acetate phthalate, hydroxypropyl cellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Rohm Pharma). Additionally, the coating material may contain conventional carriers such as plasticizers, pigments, colorants, glidants, stabilization agents, and surfactants.

III. Methods of Manufacturing

The compositions described herein can be prepared using techniques well known in the art. Multilayer tablets may be prepared by compression molding. In compression molding, the core and the one or more barrier layers are prepared separately and then compressed using a multilayer tableting press. Alternatively, the core can be prepared separately with the barrier layers added as a blend, and the composition compressed to form a tablet.

The geometric shape of the dosage forms described herein may vary depending on the type of release profile that is desired. In its simplest form, the dosage form might consist of a monolithic core. Alternatively, the core may consist of one of more layers containing one or more pharmaceutically active substances in each layer. Dosage forms of this type have been described in U.S. Pat. Nos. 5,626,874, 5,422,123 and 6,027,748 to Conte et al.

Alternatively, one or more layers may contain no active agents. Each layer may contain the same or different release-controlling materials and excipients. In another embodiment, the dosage form may be a multiparticulate system. Each particle may contain the same or different pharmaceutically active substance and the same or different release-controlling materials and other adjuvants. In a preferred dosage form, the core is multilayered, e.g. having two or three layers, one or more of which contains a pharmaceutically active substance and the other layers contain no pharmaceutically active substance. In a particularly preferred embodiment the dosage form comprises a core consisting of three layers wherein an inner layer contains a pharmaceutically active substance and the two outer layers do not contain a pharmaceutically active substance.

The formulations can be coated with a film coat that at least partially overcoats the core using techniques well known in the art. The coatings can be applied as a solid or as an aqueous suspension or organic solution. Suitable techniques for applying the coating include, but are not limited to, spray coating, pan coating, fluid bed coating, and compression coating.

Core or Central Layer

Drug and surfactant are mixed in a high shear mixer for one to five minutes, preferably two minutes. Excipients such as lactose monohydrate, povidone, methacrylic acid copolymer, and hypromellose type 2208, can be added to the mixer and mixed for five to fifteen minutes, preferably ten minutes. The binding solution can be prepared by dissolving a binding agent such as povidone in purified water and adding a surfactant such as sodium lauryl sulfate. The binding solution is added to the high shear mixer and mixed briefly, for example, from one to five minutes, preferably for about two minutes. The resulting granulation can be kneaded and transferred to a fluid bed dryer and dried. After drying, the granulation is milled. After milling, all or part of the granulation can be placed into a diffusion blender and an excipient such as colloidal silicon dioxide can be added and mixed, for example, for twenty minutes. Optionally, an excipient such as magnesium stearate can be premixed manually with 5% of the mixture and then added to the granulation mixture and mixed, for example, for ten minutes.

Barrier Layers

Excipients such as lactose monohydrate, glyceryl behenate, ferric oxide (yellow), povidone, hypromellose type 2910 (Methocel E4M), and optionally hypromellose phthalate, are added to a high shear mixer and mixed, for example, for five to fifteen minutes, preferably six minutes. Purified water is added to the mixture in step 1 and kneaded, for example, for about two minutes. The granulation can be transferred to a fluid bed dryer and dried, for example, until an LOD below 2.5% was obtained. After drying, the granulation can be milled on an oscillatory mill. After milling, one half of the granulation was placed into a diffusion blender. Colloidal silicon dioxide was added to the blender followed by the remainder of the granulation. The mixture is mixed, for example, for twenty minutes. Binder is prepared as above and added to the barrier layer.

Tableting

The central layer and the barrier layers were loaded into a HATA multi-layer tablet press and pressed to form the trilayer tablets.

Film Coat

The film coatings are applied to the table using standard techniques. In the case of an enteric coating, manufacturer directions are followed.

IV. Methods of Administration

The compositions can be administered to treat a variety of cardiovascular disorders, such as hypertension, angina, and cardiac arrhythmia. Although preferred patients are human, typically any mammal including domestic animals such as dogs and cats, may also be treated. The compositions are generally administered orally in the form of a tablet. The composition can be administered in a single dose, an escalating dose, or administered at an elevated dosage which is then decreased to a lower dosage after a particular circulating blood concentration of the compound has been achieved.

One of skill in the art would be able to choose administration protocols and determine appropriate dosing regimes based on bioavailability and half-life of the compound to be administered. Appropriate dosages of the calcium channel blockers can be determined by one of skill in the art using routine experimentation and standard techniques utilizing dosages currently approved. Intra-patient variability is known in the art depending on the severity of symptoms and dosages are commonly adjusted to exact a particular therapeutic effect in a particular patient.

For many of the disclosed compounds, appropriate dosage ranges have been established to maximize circulating concentrations of the compound and minimize side-effects. Generally, the calcium channel blocker is administered at a dosage of 0.001 to 100 mg/kg of body weight of the patient, preferably 0.01 mg to 10 mg/kg, more preferably 0.1 to 1.0 mg/kg. Preferred daily doses of a calcium channel blocker are approximately 1-100 mg, preferably 2.5 mg to 50 mg. The preferred daily dose of nisoldipine is approximately 5 mg to 50 mg.

A. Pharmacokinetic Parameters

The compositions described herein provide an increased bioavailability (as measured by area under the drug plasma concentration-time curve (AUC)) as compared to the same dose of calcium channel blocker in a reference formulation containing a slow release core and an immediate release coating (coat-core). In a preferred embodiment, the compositions provide an increase in bioavailability of nisoldipine as compared to the same dose of drug in SULAR®. In another embodiment, the compositions contain a reduced dose of nisoldipine, but exhibit a similar pharmacokinetic profile as SULAR®.

For example, a trilayer tablet containing 40 mg nisoldipine (Formulation A) exhibited a roughly 16% increase in the $AUC_{last}$ compared to SULAR® 40 mg. This suggests that the dose of nisoldipine in the trilayer tablet can be reduced by approximately 16% (i.e. to 34 mg) and still provide an effective amount of the drug. Accordingly, the 10 mg, 20 mg, 30 mg, and 40 mg dosage strengths of SULAR® can be replaced with reduced, bioequivalent dosage strengths (for example, 8.5 mg, 17 mg, 25.5 mg, and 34 mg) of the compositions defined herein. This may result in lower manufacturing costs due to the lower doses required to obtain the desired therapeutic effect.

In another embodiment, the compositions described herein contain one or more controlled release elements in an amount effective to provide a controlled release of the calcium channel blocker, the composition providing a $T_{max}$ of the calcium channel blocker from about 3.85 to about 15 hours and an $AUC_{last}$ of the calcium channel blocker from about 38 hr*ng/ml to about 87 hr*ng/ml under fasting conditions based on a 40 mg dose.

In yet another embodiment, the compositions described herein contain one or more controlled release elements in an amount effective to provide a controlled release of the calcium channel blocker, the composition providing a $T_{max}$ of the calcium channel blocker from about 3.85 to about 15 hours and a $C_{max}$ of the calcium channel blocker from about 1.5 to about 6.5 ng/mL under fasting conditions based on a 40 mg dose.

In yet another embodiment, the compositions described herein contain one or more controlled release elements in an amount effective to provide a controlled release of the calcium channel blocker, the composition providing a $AUC_{inf}$ of the calcium channel blocker from about 41.8 hr*ng/ml to about 103.8 hr*ng/ml under fasting conditions, preferably from about 38 hr*ng/ml to about 87 hr*ng/ml under fasting conditions based on a 40 mg dose.

In yet another embodiment, the compositions described herein contain one or more controlled release elements in an amount effective to provide a controlled release of the calcium channel blocker, the composition providing a $C_{max}$ of the calcium channel blocker from about 0.23 to about 7.35 ng/mL under fasting conditions based on a 34 mg dose.

In yet another embodiment, the compositions described herein contain one or more controlled release elements in an amount effective to provide a controlled release of the calcium channel blocker, the composition providing a $T_{max}$ of the calcium channel blocker from about 4 to about 14.5, preferably from about 8 to about 10 hours under fasting conditions based on a 34 mg dose.

In yet another embodiment, the compositions described herein contain one or more controlled release elements in an amount effective to provide a controlled release of the calcium channel blocker, the composition providing a $AUC_{inf}$ of the calcium channel blocker from about 27 hr*ng/ml to about 102 hr*ng/ml under fasting conditions, preferably from about 28 hr*ng/ml to about 97.5 hr*ng/ml under fasting conditions based on a 34 mg dose.

In yet another embodiment, the compositions described herein contain one or more controlled release elements in an amount effective to provide a controlled release of the calcium channel blocker, the composition providing a $C_{max}$ of the calcium channel blocker from about 0.17 to about 5.5 ng/mL under fasting conditions based on a 25.5 mg dose.

In yet another embodiment, the compositions described herein contain one or more controlled release elements in an amount effective to provide a controlled release of the calcium channel blocker, the composition providing a $AUC_{inf}$ of the calcium channel blocker from about 21 hr*ng/ml to about 76.5 hr*ng/ml under fasting conditions, preferably from about 20 hr*ng/ml to about 73 hr*ng/ml under fasting conditions based on a 25.5 mg dose.

In yet another embodiment, the compositions described herein contain one or more controlled release elements in an amount effective to provide a controlled release of the calcium channel blocker, the composition providing a $C_{max}$ of the calcium channel blocker from about 0.11 to about 3.66 ng/mL under fasting conditions based on a 17 mg dose.

In yet another embodiment, the compositions described herein contain one or more controlled release elements in an amount effective to provide a controlled release of the calcium channel blocker, the composition providing a $AUC_{inf}$ of the calcium channel blocker from about 14 hr*ng/ml to about 51 hr*ng/ml under fasting conditions, preferably from about 13 hr*ng/ml to about 48 hr*ng/ml under fasting conditions based on a 17 mg dose.

In yet another embodiment, the compositions described herein contain one or more controlled release elements in an amount effective to provide a controlled release of the calcium channel blocker, the composition providing a $C_{max}$ of the calcium channel blocker from about 0.014 to about 1.7 ng/mL under fasting conditions based on a 8.5 mg dose.

In yet another embodiment, the compositions described herein contain one or more controlled release elements in an amount effective to provide a controlled release of the calcium channel blocker, the composition providing a $T_{max}$ of the calcium channel blocker from about 4.5 to about 12.7, preferably from about 8 to about 10 hours under fasting conditions based on a 8.5 mg dose.

In yet another embodiment, the compositions described herein contain one or more controlled release elements in an amount effective to provide a controlled release of the calcium channel blocker, the composition providing a $AUC_{inf}$ of the calcium channel blocker from about 4.3 hr*ng/ml to about 23.25 hr*ng/ml under fasting conditions, preferably from about 4.1 hr*ng/ml to about 22.4 hr*ng/ml under fasting conditions based on a 8.5 mg dose.

In yet another embodiment, the compositions described herein contain one or more controlled release elements in an amount effective to provide a controlled release of the calcium channel blocker, the composition providing a $C_{max}$ of the calcium channel blocker from about 5 to about 13 ng/mL under fed conditions when the dose of the calcium channel blocker is less than 40 mg.

In yet another embodiment, the compositions described herein contain one or more controlled release elements in an amount effective to provide a controlled release of the calcium channel blocker, the composition providing a $T_{max}$ of the calcium channel blocker from about 3.7 to about 8.6, under fed conditions when the dose of the calcium channel blocker is less than 40 mg.

In yet another embodiment, the compositions described herein contain one or more controlled release elements in an amount effective to provide a controlled release of the calcium channel blocker, the composition providing a $AUC_{inf}$ of the calcium channel blocker from about 31 hr*ng/ml to about 66 hr*ng/ml under fasting conditions, preferably from about 31 hr*ng/ml to about 62.5 hr*ng/ml under fed conditions when the dose of the calcium channel blocker is less than 40 mg.

The present invention will be further understood by reference to the following non-limiting examples.

EXAMPLES

Example 1

Trilayer Tablets Containing 40 mg of Nisoldipine

Three different formulations, each of which contained 40 mg of Nisoldipine, were prepared. The formulations are identified as Formulation A, Formulation B, and Formulation C and are described in Tables 1-3. Formulation C was coated with an enteric coating (5% weight gain) containing a combination of Eudragit® S100 (methacrylic acid copolymer type B) and Eudragit® L100 (methacrylic acid copolymer type A). Formulations A and B were coated with an OPADRY® II seal coat available from Colorcon, West Point, Pa.

TABLE 1

Composition of Formulation A

| Ingredient | First Barrier Layer (mg/tab) | Core (mg/tab) | Second Barrier Layer (mg/tab) | Total (mg) | Weight % (of the tablet) |
|---|---|---|---|---|---|
| Nisoldipine | | 40.00 | | 40.00 | 7.1 |
| Lactose Monohydrate, NF | 76.5 | 32.35 | 57.375 | 166.23 | 29.5 |
| Ferric Oxide, NF (yellow) | 0.20 | | 0.15 | 0.35 | 0.1 |
| Hypromellose, USP, type 2208 (Methocel ® K4M) | | 53.65 | | 53.65 | 9.5 |
| Sodium lauryl sulfate, NF | | 50.00 | | 50.00 | 8.9 |
| Methacrylic Acid Copolymer, Type B, NF (S) | | 21.40 | | 21.40 | 3.8 |
| Hypromellose Phthalate, NF | 26.5 | | 19.875 | 46.38 | 8.2 |
| Glyceryl Behenate, NF | 36.8 | | 27.6 | 64.40 | 11.4 |
| Povidone, USP (29/32) | 7.00 | 10.70 | 5.25 | 22.95 | 4.1 |
| Hypromellose, USP, type 2910 (Methocel ® E5) | | | 37.5 | 37.50 | 6.7 |
| Hypromellose, USP, type 2910 (Methocel ® E50LV) | 50.0 | | | 50.0 | 8.9 |
| Magnesium Stearate, NF (vegetable) | 2.00 | 3.80 | 1.5 | 7.30 | 1.3 |
| Colloidal Silicon Dioxide, NF | 1.00 | 1.10 | 0.75 | 2.85 | 0.5 |
| Totals | 200 | 213 | 150 | 563 | 100% |

TABLE 2

Composition of Formulation B

| Ingredient | First Barrier Layer (mg/tab) | Core (mg/tab) | Second Barrier Layer (mg/tab) | Total (mg) | Weight % (of the tablet) |
|---|---|---|---|---|---|
| Nisoldipine | | 40.00 | | 40.00 | 7.10 |
| Lactose Monohydrate, NF | 76.50 | 32.35 | 57.375 | 166.23 | 29.52 |
| Ferric Oxide, NF (yellow) | 0.20 | | 0.15 | 0.35 | 0.06 |
| Hypromellose, USP, type 2208 (Methocel ® K4M) | | 53.65 | | 53.65 | 9.53 |
| Hypromellose, USP, type 2910 (Methocel ® E4M) | 76.50 | | 57.375 | 133.88 | 23.78 |
| Sodium lauryl sulfate, NF | | 50.00 | | 50.00 | 8.88 |
| Methacrylic Acid Copolymer, Type B, NF (S) | | 21.40 | | 21.40 | 3.80 |
| Glyceryl Behenate, NF | 36.80 | | 27.60 | 64.40 | 11.44 |
| Povidone, USP (29/32) | 7.00 | 10.70 | 5.25 | 22.95 | 4.08 |
| Magnesium Stearate, NF (vegetable) | 2.00 | 3.80 | 1.50 | 7.30 | 1.30 |
| Colloidal Silicon Dioxide, NF | 1.00 | 1.10 | 0.75 | 2.85 | 0.51 |
| Totals | 200.00 | 213.00 | 150.00 | 563.00 | 100% |

TABLE 3

Composition of Formulation C

| Ingredient | First Barrier layer (mg/tab) | Core (mg/tab) | Second Barrier layer (mg/tab) | Film Coat (mg/tab) | Total (mg) | Weight % (of the tablet) |
|---|---|---|---|---|---|---|
| Nisoldipine | | 40.00 | | | 40.00 | 6.14 |
| Lactose Monohydrate, NF | 76.5 | 32.35 | 57.375 | | 166.23 | 25.53 |
| Ferric Oxide, NF (yellow) | 0.20 | | 0.15 | | 0.35 | 0.05 |
| Hypromellose, USP, type 2208 (Methocel ® K4M) | | 53.65 | | | 53.65 | 8.24 |
| Sodium lauryl sulfate, NF | | 50.00 | | | 50.00 | 7.68 |
| Methacrylic Acid Copolymer, Type B, NF (S) | | 21.40 | | 25.45 | 46.85 | 7.20 |
| Hypromellose Phthalate, NF | 26.5 | | 19.875 | | 46.38 | 7.12 |
| Glyceryl Behenate, NF | 36.8 | | 27.6 | | 64.40 | 9.89 |
| Povidone, USP (29/32) | 7.00 | 10.70 | 5.25 | | 22.95 | 3.53 |
| Hypromellose, USP, type 2910 (Methocel ® E5) | | | 37.5 | | 37.50 | 5.76 |
| Hypromellose, USP, type 2910 (Methocel ® E50LV) | 50.0 | | | | 50.00 | 7.68 |
| Magnesium Stearate, NF (vegetable) | 2.00 | 3.80 | 1.5 | | 7.30 | 1.12 |
| Colloidal Silicon Dioxide, NF | 1.00 | 1.10 | 0.75 | | 2.85 | 0.44 |
| Methacrylic Acid Copolymer, Type A, NF | | | | 25.49 | 25.49 | 3.92 |
| Triethyl Citrate, USP | | | | 35.86 | 35.86 | 5.51 |
| Potassium Hydroxide, NF | | | | 1.21 | 1.21 | 0.19 |
| Totals | 200.00 | 213.00 | 150.00 | 88.00 | 651.00 | 100% |

The formulations described above were prepared as follows:

Core or Central Layer

1. Nisoldipine and sodium lauryl sulfate were mixed in a high shear mixer for two minutes. Lactose monohydrate, povidone, methacrylic acid copolymer (type B), and hypromellose type 2208 (Methocel K4M) were added to the mixer and mixed for ten minutes.

2. The binding solution was prepared by dissolving povidone in purified water and adding sodium lauryl sulfate. The mixture was mixed in a suitable tank and left to rest until defoaming was complete.

3. The binding solution was added to the high shear mixer containing the mixture of step 1 and mixed briefly for two minutes. The resulting granulation was kneaded and transferred to a fluid bed dryer and dried until an LOD below 2.5% was obtained. After drying, the granulation was milled with an oscillatory mill.

4. After milling, one half of the granulation was placed into a diffusion blender. Colloidal silicon dioxide was added to the blender followed by the remainder of the granulation. The mixture was mixed for twenty minutes.

5. Magnesium stearate was premixed manually with 5% of the mixture from step 4. The premix was added to the granulation in the Bohle blender and mixed for ten minutes.

Barrier Layers

1. Lactose monohydrate, glyceryl behenate, ferric oxide (yellow), povidone, hypromellose type 2910 (Methocel E4M), and optionally hypromellose phthalate, were added to a high shear mixer and mixed for six minutes.

2. Purified water was added to the mixture in step 1 and kneaded for about two minutes.

3. The granulation was transferred to a fluid bed dryer and dried until an LOD below 2.5% was obtained. After drying, the granulation was milled on an oscillatory mill.

4. After milling, one half of the granulation was placed into a diffusion blender. Colloidal silicon dioxide was added to the blender followed by the remainder of the granulation. The mixture was mixed for twenty minutes.

5. Magnesium stearate was premixed manually with 5% of the mixture from step 4. The premix was added to the granulation in a diffusion blender and mixed for ten minutes.

Tableting

The central layer and the barrier layers were loaded into a HATA multi-layer tablet press and pressed to form the trilayer tablets.

Film Coat

The film coatings are applied at a target of 5% weight gain on a 563 mg tablet. Opadry® II film coating compositions were obtained from Colorcon, West Point, Pa. Four different coating compositions were used: 49B97383 Beige, 49B397382 Beige, 49B92439 Yellow, and 49B97379 Beige. All of the film coat compositions contain polydextrose FCC, HPMC 2910/hypromellose 3cP, HPMC 2910/hypromellose 6cP, titanium dioxide, HPMC 2910/hypromellose 15cP, macrogol/PEG, iron oxide yellow, and carnauba wax. The compositions vary in the presence or absence of iron oxide black, iron oxide red, and FD&C yellow #5/Tartrazine Aluminum Lake. The tablets were coated as directed by the manufacturer.

Enteric Coating (Formulation C)

1. Potassium hydroxide was dissolved in purified water with agitation to form a 1N solution.

2. Methacrylic acid copolymer type B (Eudragit S100) was added slowly to a vortex of purified water and mixed until dissolved.

3. The 1N potassium hydroxide solution of step 1 was added to the solution of step 2 and the mixture was stirred gently.

4. Triethyl citrate was added to the solution of step 3 and stirred until the mixture was homogeneous.

5. Steps 1-4 were repeated using methacrylic acid copolymer type A (Eudragit L100) to form a homogeneous mixture.

6. The solution of step 4 was added to a mixing vessel and stirred slowly. The solution of step 5 was added to the vessel and the mixture was stirred for the required period of time.

7. The tablets of Formulation C were coated with the coating layer using a Glatt pan coater.

Example 2

Relative Bioavailability Study of Nisoldipine 40 mg Extended Release Tablets Under Fasting Conditions The pharmacokinetic parameters of formulations A-C described in Example 1 were compared to those of a reference formulation (Formulation D). The reference formulation was SULAR® Nisoldipine Extended Release (40 mg). SULAR® is a coat-core formulation consisting of a core containing Nisoldipine, coated with an immediate release coating which also contains Nisoldipine. The components of SULAR®, and their concentrations, are given in Table 4.

The objective of this single-dose, open-label, randomized study was to compare, under fasting conditions, the rate of absorption and oral bioavailability of a test formulation of nisoldipine 40 mg extended-release tablets described in Example 1 to an equivalent oral dose of the commercially available reference product, SULAR® 40 mg extended-release tablets, when administered to healthy subjects.

TABLE 4

Composition of SULAR® (Formulation D)

| Ingredient | Coat (mg/tab) | Core (mg/tab) | Film Coat (mg/tab) | Total (mg/tab) | Weight % (of the tablet) |
|---|---|---|---|---|---|
| Nisoldipine | 32.0 | 8.0 | | 40.0 | 12.27 |
| Crospovidone, NF | | 5.0 | | 5.0 | 1.53 |
| Lactose Monohydrate, NF | 87.5 | 4.0 | | 91.5 | 28.07 |
| Magnesium Stearate, NF | 1.0 | 0.2 | | 1.2 | 0.37 |
| Corn Starch, NF | | 10.0 | | 10.0 | 3.07 |
| Microcrystalline Cellulose, NF | | 17.2 | | 17.2 | 5.28 |
| Povidone, USP | | 1.8 | | 1.8 | 0.55 |
| Sodium lauryl sulfate, NF | | 0.8 | | 0.8 | 0.25 |
| Hydroxypropyl-cellulose, medium viscosity, NF | 84.5 | | | 84.5 | 25.92 |
| Hydroxypropyl-cellulose, low viscosity, NF | 63.0 | | | 63.0 | 19.33 |
| Hypromellose, USP | | | 6.6 | 6.6 | 2.02 |
| Ferric Oxide, NF (red) | | | 0.11 | 0.11 | 0.03 |
| Ferric Oxide, NF (yellow) | | | 0.99 | 0.99 | 0.30 |
| Macrogol, NF | | | 2.2 | 2.2 | 0.67 |
| Titanium Dioxide, USP | | | 1.1 | 1.1 | 0.34 |
| Totals | 268.0 | 47.0 | 11.0 | 326.00 | 100.00 |

Thirty-two healthy adults participated in the comparison of the three formulations of nisoldipine 40 mg tablets described in Example 1 versus SULAR®. 31 subjects completed the study. Subjects received the assigned treatment during the first period and received the alternate treatment during the subsequent periods according to the randomization scheme. Dosing days were separated by a washout period of at least 7 days. An equal number of subjects were randomly assigned to each possible sequence of treatments. Drug administration consisted of an oral dose of the formulations described in Example 1 and SULAR® under fasting conditions.

Blood samples were drawn prior to dosing (pre-dose) at 1, 1.5, 2, 3, 4, 6, 7.5, 9, 10.5, 12, 14, 16, 18, 20, 21, 23, 24, 26, 28, 30, 36, and 48 hours post-dose.

Plasma samples were analyzed using a validated LC-MS-MS procedure with a lower limit of quantification of 0.0150 ng/mL for nisoldipine. Data were stored in the Watson LIMS System (Thermo Electron Corporation Version 6.4.0.02).

Data from all subjects who completed the study were to be included in the pharmacokinetic and statistical analyses. The concentration-time data were transferred from Watson directly to WinNonlin (Enterprise Version 4.0, Pharsight, Cary, N.C.) using the Custom Query Builder option for analysis. Data were analyzed by noncompartmental methods in WinNonlin.

Concentration-time data that were BLQ (<0.0150 ng/mL) were treated as zero (0.00 ng/mL) in the data summarization and descriptive statistics. In the pharmacokinetic analysis, BLQ concentrations were treated as zero from time-zero up to the time at which the first quantifiable concentration was observed; embedded and/or terminal BLQ concentrations were treated as "missing". Full precision concentration data were used for all pharmacokinetic and statistical analyses.

The following pharmacokinetic parameters were calculated for each subject and period: peak concentration in plasma ($C_{max}$), time to peak concentration ($T_{max}$), elimination rate constant ($\lambda_z$), terminal half-life ($T_{1/2}$), area under the concentration-time curve from time-zero to the time of the last quantifiable concentration ($AUC_{last}$), and area under the plasma concentration time curve from time-zero extrapolated to infinity ($AUC_{inf}$), and are shown in Table 5. Formulation A was chosen for further testing.

A comparison of the pharmacokinetic parameters for Formulation A and the reference formulation (Formulation D) are shown in Table 6. Table 7 shows the statistical analysis of the non-transformed pharmacokinetic parameters of nisoldipine after Formulation A and the reference product (Formulation D).

Analysis of variance (ANOVA) and the Schuirmann's two one-sided t-test procedures at the 5% significance level were applied to the log-transformed pharmacokinetic exposure parameters, $C_{max}$, $AUC_{last}$, and $AUC_{inf}$. The 90% confidence interval for the difference between the means of the test product and the reference product was calculated. Bioequivalence was declared if the lower and upper confidence intervals of the log-transformed parameters were within 80%-125%.

FIG. 1 shows the mean nisoldipine concentration versus time (in hours) for three test formulations (treatments A, B, and C) and the reference product SULAR® (treatment D) under fasting conditions. The reference formulation exhibited a maximum mean nisoldipine concentration at approximately 6 hours. In contrast, Formulations A and B exhibited a maximum mean nisoldipine concentration at approximately 12 hours, while Formulation C exhibited a maximum mean nisoldipine concentration at just over 24 hours.

TABLE 5

Pharmacokinetic Parameters of Nisoldipine After Oral Administration

| Parameter | Treatment A: Test Formulation A | | | | Treatment B: Test Formulation B | | | | Treatment C: Test Formulation C | | | | Treatment D: Reference Product | | | |
|---|---|---|---|---|---|---|---|---|---|---|---|---|---|---|---|---|
| | n | Mean | SD | CV % | n | Mean | SD | CV % | n | Mean | SD | CV % | n | Mean | SD | CV % |
| $T_{max}$ (hr) | 31 | 9.42 | 5.57 | 59.16 | 31 | 16.44 | 9.49 | 57.71 | 31 | 20.57 | 9.47 | 46.05 | 32 | 8.12 | 7.34 | 90.47 |
| $T_{lag}$ (hr) | 31 | 0.03 | 0.18 | 556.78 | 31 | 3.31 | 4.03 | 122.00 | 31 | 0.00 | 0.00 | NC | 32 | 0.13 | 0.71 | 565.69 |
| $C_{max}$ (ng/mL) | 31 | 4.03 | 2.51 | 62.22 | 31 | 2.83 | 1.13 | 39.96 | 31 | 2.75 | 1.47 | 53.54 | 32 | 3.49 | 1.52 | 43.42 |
| $AUC_{last}$ (hr*ng/mL) | 31 | 62.61 | 24.53 | 39.18 | 31 | 48.92 | 24.65 | 50.39 | 31 | 51.86 | 30.68 | 59.16 | 32 | 53.46 | 23.26 | 43.51 |
| $AUC_{inf}$ (hr*ng/mL) | 29 | 72.84 | 30.97 | 42.52 | 26 | 61.28 | 34.27 | 55.93 | 25 | 56.11 | 36.51 | 65.07 | 30 | 68.21 | 43.33 | 63.52 |
| $AUC_{Extrap}$ (%) | 29 | 12.17 | 11.27 | 92.55 | 26 | 12.64 | 13.45 | 106.43 | 25 | 11.94 | 14.26 | 119.38 | 30 | 14.00 | 15.84 | 113.11 |
| $\lambda_z$ (hr$^{-1}$) | 29 | 0.0600 | 0.0247 | 41.06 | 26 | 0.0691 | 0.0337 | 48.78 | 25 | 0.0739 | 0.0299 | 40.53 | 30 | 0.0580 | 0.0238 | 41.02 |
| $T_{1/2}$ (hr) | 29 | 14.23 | 8.83 | 62.01 | 26 | 12.92 | 8.89 | 68.83 | 25 | 12.78 | 11.20 | 87.63 | 30 | 17.57 | 18.77 | 106.82 |
| $T_{last}$ (hr) | 31 | 48.07 | 0.26 | 0.54 | 31 | 48.04 | 0.06 | 0.12 | 31 | 47.09 | 3.84 | 8.16 | 32 | 48.03 | 0.08 | 0.17 |
| $C_{last}$ (ng/mL) | 31 | 0.470 | 0.370 | 78.77 | 31 | 0.491 | 0.441 | 89.67 | 31 | 0.532 | 0.533 | 100.15 | 32 | 0.441 | 0.408 | 92.39 |
| MRT (hr) | 29 | 25.40 | 12.19 | 47.98 | 26 | 28.45 | 13.68 | 48.08 | 25 | 27.89 | 16.00 | 57.37 | 30 | 28.61 | 24.66 | 86.18 |

TABLE 6

Pharmacokinetic Parameters of Nisoldipine After Oral Administration

| Parameter | Treatment A: Test Formulation #1 | | | | Treatment D: Reference Product | | | |
|---|---|---|---|---|---|---|---|---|
| | n | Mean | SD | CV % | n | Mean | SD | CV % |
| $T_{max}$ (hr) | 31 | 9.42 | 5.57 | 59.16 | 32 | 8.12 | 7.34 | 90.47 |
| $T_{lag}$ (hr) | 31 | 0.03 | 0.18 | 556.78 | 32 | 0.13 | 0.71 | 565.69 |
| $C_{max}$ (ng/mL) | 31 | 4.03 | 2.51 | 62.22 | 32 | 3.49 | 1.52 | 43.42 |
| $AUC_{last}$ (hr*ng/mL) | 31 | 62.61 | 24.53 | 39.18 | 32 | 53.46 | 23.26 | 43.51 |
| $AUC_{inf}$ (hr*ng/mL) | 29 | 72.84 | 30.97 | 42.52 | 30 | 68.21 | 43.33 | 63.52 |
| $AUC_{Extrap}$ (%) | 29 | 12.17 | 11.27 | 92.55 | 30 | 14.00 | 15.84 | 113.11 |

TABLE 6-continued

Pharmacokinetic Parameters of Nisoldipine After Oral Administration

|  | Treatment A: Test Formulation #1 | | | | Treatment D: Reference Product | | | |
|---|---|---|---|---|---|---|---|---|
| Parameter | n | Mean | SD | CV % | n | Mean | SD | CV % |
| $\lambda_z$ (hr$^{-1}$) | 29 | 0.0600 | 0.0247 | 41.06 | 30 | 0.0580 | 0.0238 | 41.02 |
| $T_{1/2}$ (hr) | 29 | 14.23 | 8.83 | 62.01 | 30 | 17.57 | 18.77 | 106.82 |
| $T_{last}$ (hr) | 31 | 48.07 | 0.26 | 0.54 | 32 | 48.03 | 0.08 | 0.17 |
| $C_{last}$ (ng/mL) | 31 | 0.470 | 0.370 | 78.77 | 32 | 0.441 | 0.408 | 92.39 |
| MRT (hr) | 29 | 25.40 | 12.19 | 47.98 | 30 | 28.61 | 24.66 | 86.18 |

TABLE 7

Statistical Analysis of the Non-Transformed Pharmacokinetic Parameters of Nisoldipine After Formulation A and the Reference Product

| Dependent Variable | Least Squares Mean | | Ratio (%) (Test/Reference) | 90% Confidence Interval | | Power |
|---|---|---|---|---|---|---|
|  | Test | Reference |  | Lower | Upper |  |
| $C_{max}$ | 4.0176 | 3.4943 | 114.98 | 96.07 | 133.89 | 0.5385 |
| $AUC_{last}$ | 62.1910 | 53.4555 | 116.34 | 102.23 | 130.46 | 0.7550 |
| $AUC_{inf}$ | 67.0708 | 63.9262 | 104.92 | 80.56 | 129.28 | 0.3847 |
| $T_{max}$ | 9.3247 | 8.1156 | 114.90 | 77.51 | 152.29 | 0.2270 |
| $T_{lag}$ | 0.0252 | 0.1250 | 20.19 | −659.85 | 700.23 | 0.1004 |
| $\lambda_z$ | 0.0651 | 0.0644 | 100.99 | 83.73 | 118.25 | 0.6044 |
| $T_{1/2}$ | 11.9103 | 14.3679 | 82.90 | 55.16 | 110.63 | 0.3241 |
| MRT | 22.5857 | 24.0788 | 93.80 | 70.83 | 116.77 | 0.4161 |

TABLE 8

Statistical Analysis of the Log-Transformed Systemic Exposure Parameters of Nisoldipine after Test Formulation #1 and Reference Product

| Dependent Variable | LS Mean[a] | | Geometric Mean[b] | | Ratio (%)[c] (Test/Ref) | 90% CI[d] | | Power | ANOVA CV % |
|---|---|---|---|---|---|---|---|---|---|
|  | Test | Ref | Test | Ref |  | Lower | Upper |  |  |
| $\ln(C_{max})$ | 1.2424 | 1.1624 | 3.4639 | 3.1975 | 108.33 | 90.47 | 129.72 | 0.6537 | 44.97 |
| $\ln(AUC_{last})$ | 4.0571 | 3.8763 | 57.8035 | 48.2441 | 119.81 | 100.89 | 142.29 | 0.6894 | 42.68 |
| $\ln(AUC_{inf})$ | 4.1247 | 3.9602 | 61.8507 | 52.4682 | 117.88 | 90.92 | 152.85 | 0.4087 | 54.05 |

[a]Least Squares Mean for the Test Formulation #1 (Test) and Reference Product (Ref)
[b]Geometric Mean based on LS Mean of log-transformed parameter values
[c]Ratio(%) = Geometric Mean (Test)/Geometric Mean (Ref)
[d]90% Confidence Interval
Note:
Statistical analysis based n = 31 for $C_{max}$, $AUC_{last}$ and n = 21 for $AUC_{inf}$ Example 3

Relative Bioavailability study of Nisoldipine 40 mg Extended Release Tablets Under Fed Conditions The objective of this study was to compare the food effect of the Formulation A described in Example versus the food effect of the SULAR® market formulation. To determine the food effects for Formulation A and SULAR® the pharmacokinetic data for these two formulations from Example 2 under fasting conditions were used as a reference. The same 32 subjects from Example 2 were enrolled in the food effect study.

Twenty-six (26) subjects completed the study. In the first periods subjects received the assigned treatment and received the alternate treatment during the subsequent period according to the randomization scheme. Dosing days were separated by a washout period of at least 7 days. An equal number of subjects were randomly assigned to each possible sequence of treatments. Blood samples were taken and analyzed as described in Example 2. Table 9 shows pharmacokinetic data for Formulation A (Treatment E) and the reference formulation (SULAR®, 40 mg extended-release) under fed conditions. Table 10 shows analysis of the non-transformed pharmacokinetic parameters of nisoldipine after test formulation A (Treatment E) and reference product (Treatment F) under fed conditions. Table 11 shows statistical analysis of the log-transformed systemic parameters of nisoldipine after test formulation A (Treatment E) and the reference product (Treatment F) under fed conditions.

TABLE 9

Pharmacokinetic Parameters of Nisoldipine After Oral Administration Under Fed Conditions

| Parameter | Treatment E: Test Formulation #1 | | | | Treatment F: Reference Product | | | |
|---|---|---|---|---|---|---|---|---|
| | n | Mean | SD | CV % | n | Mean | SD | CV % |
| $T_{max}$ (hr) | 26 | 6.14 | 2.42 | 39.48 | 26 | 6.29 | 3.36 | 53.36 |
| $T_{lag}$ (hr) | 26 | 0.08 | 0.27 | 353.27 | 26 | 0.12 | 0.33 | 282.37 |
| $C_{max}$ (ng/mL) | 26 | 9.08 | 3.95 | 43.53 | 26 | 10.1 | 8.33 | 82.11 |
| $AUC_{last}$ (hr*ng/mL) | 26 | 46.74 | 15.75 | 33.70 | 26 | 49.90 | 30.16 | 60.44 |
| $AUC_{inf}$ (hr*ng/mL) | 26 | 48.92 | 16.91 | 34.57 | 26 | 52.88 | 30.69 | 58.04 |
| $AUC_{Extrap}$ (%) | 26 | 4.16 | 2.67 | 64.19 | 26 | 6.48 | 7.13 | 110.07 |
| $\lambda_z$ (hr$^{-1}$) | 26 | 0.0547 | 0.0126 | 23.03 | 26 | 0.0539 | 0.0157 | 29.12 |
| $T_{1/2}$ (hr) | 26 | 13.30 | 2.88 | 21.63 | 26 | 14.61 | 6.84 | 46.77 |
| $T_{last}$ (hr) | 26 | 48.03 | 0.08 | 0.18 | 26 | 48.01 | 0.27 | 0.57 |
| $C_{last}$ (ng/mL) | 26 | 0.104 | 0.0698 | 66.92 | 26 | 0.130 | 0.0821 | 63.15 |
| MRT (hr) | 26 | 13.64 | 3.20 | 23.49 | 26 | 16.39 | 7.28 | 44.42 |

TABLE 10

Statistical Analysis of the Non-Transformed Pharmacokinetic Parameters of Nisoldipine after Test Formulation A (Treatment E) and Reference Product (Treatment F) under Fed Conditions

| Dependent Variable | Least Squares Mean | | Ratio (%) (E/F) | 90% Confidence Interval | | Power |
|---|---|---|---|---|---|---|
| | Treatment E | Treatment F | | Lower | Upper | |
| $C_{max}$ | 9.0795 | 10.1485 | 89.47 | 63.66 | 115.27 | 0.3547 |
| $AUC_{last}$ | 46.7358 | 49.9013 | 93.66 | 77.56 | 109.75 | 0.6596 |
| $AUC_{inf}$ | 48.9166 | 52.8817 | 92.50 | 77.06 | 107.95 | 0.6910 |
| $T_{max}$ | 6.1372 | 6.2904 | 97.56 | 81.34 | 113.79 | 0.6534 |
| $T_{lag}$ | 0.0769 | 0.1154 | 66.67 | −65.04 | 198.37 | 0.1101 |
| $\lambda_z$ | 0.0547 | 0.0539 | 101.32 | 91.40 | 111.25 | 0.9523 |
| $T_{1/2}$ | 13.2983 | 14.6139 | 91.00 | 75.23 | 106.76 | 0.6754 |
| MRT | 13.6435 | 16.3926 | 83.23 | 67.60 | 98.85 | 0.6822 |

TABLE 11

Statistical Analysis of the Log-Transformed Systemic Exposure Parameters of Nisoldipine after Test Formulation #1 (Treatment E) and the Reference Product (Treatment F) under Fed Conditions

| Dependent Variable | LS Mean[a] | | Geometric Mean[b] | | Ratio (%)[c] (E/F) | 90% CI[d] | | Power | ANOVA CV % |
|---|---|---|---|---|---|---|---|---|---|
| | Treatment E | Treatment F | Treatment E | Treatment F | | Lower | Upper | | |
| $\ln(C_{max})$ | 2.1192 | 2.0365 | 8.3246 | 7.6641 | 108.62 | 87.54 | 134.78 | 0.5239 | 47.94 |
| $\ln(AUC_{last})$ | 3.7901 | 3.7689 | 44.2614 | 43.3308 | 102.15 | 90.67 | 115.08 | 0.9256 | 25.53 |
| $\ln(AUC_{inf})$ | 3.8330 | 3.8390 | 46.2024 | 46.4782 | 99.41 | 88.59 | 111.55 | 0.9389 | 24.65 |

[a]Least Squares Mean for the Test Formulation #1 (Test) and Reference Product (Ref)
[b]Geometric Mean based on LS Mean of log-transformed parameter values
[c]Ratio(%) = Geometric Mean (Test)/Geometric Mean (Ref)
[d]90% Confidence Interval

Example 4

Trilayer Tablets Containing a Nisoldipine Core and Two Barrier Layers

Table 5 shows that the $AUC_{last}$ for formulation A is approximately 17% higher than the $AUC_{last}$ for the reference formulation having the same dosage of nisoldipine. This suggests that the dose of nisoldipine in formulation A can be reduced by approximately 16% and still exhibit a pharmacokinetic profile similar to the reference formulation.

Formulations containing 8.5, 17, 25.5, and 34 mg of Nisoldipine in the core were prepared based on the procedures described in Example 1. These dosages represent approximately 16% less than 10 mg, 20 mg, 30 mg, and 40 mg, respectively. The components of each formulation, and their concentrations, are shown in Tables 10-13.

TABLE 12

| | Nisoldipine Multilayer Tablet Formulations | | | | | | | |
|---|---|---|---|---|---|---|---|---|
| | 8.5 mg Prototype B | | 17 mg Prototype A | | 25.5 mg | | 34 mg | |
| Ingredients | mg/tab | % | mg/tab | % | mg/tab | % | mg/tab | % |
| | 04B4 barrier | | | | | | | |
| Methocel E5 | 17.50 | 25.00 | 25.00 | 25.00 | 37.50 | 25.00 | 37.50 | 25.00 |
| HPMC Phthalate HP50 | 9.28 | 13.25 | 13.25 | 13.25 | 19.88 | 13.25 | 19.88 | 13.25 |
| Lactose pulvis H2O | 26.85 | 38.35 | 38.35 | 38.35 | 57.53 | 38.35 | 57.53 | 38.35 |
| Compritol 888 ATO | 12.88 | 18.40 | 18.40 | 18.40 | 27.60 | 18.40 | 27.60 | 18.40 |
| Plasdone K29-32 | 2.45 | 3.50 | 3.50 | 3.50 | 5.25 | 3.50 | 5.25 | 3.50 |
| Mg stearate | 0.70 | 1.00 | 1.00 | 1.00 | 1.50 | 1.00 | 1.50 | 1.00 |
| Aerosil 200 | 0.35 | 0.50 | 0.50 | 0.50 | 0.75 | 0.50 | 0.75 | 0.50 |
| Total | 70.00 | 100.00 | 100.00 | 100.00 | 150.00 | 100.00 | 150.00 | 100.00 |
| | Core (Active Layer) | | | | | | | |
| Nisoldipine | 8.50 | 12.07 | 17.00 | 12.07 | 25.50 | 11.97 | 34.00 | 15.96 |
| Lactose H2O | 14.44 | 20.51 | 52.44 | 37.24 | 76.02 | 35.69 | 48.00 | 22.54 |
| Methocel K4M | 27.18 | 38.61 | 30.80 | 21.88 | 42.60 | 20.00 | 51.50 | 24.18 |
| Eudragit S100 | 5.35 | 7.60 | 10.70 | 7.60 | 21.40 | 10.05 | 21.40 | 10.05 |
| Plasdone | 2.68 | 3.80 | 5.35 | 3.80 | 10.70 | 5.02 | 10.70 | 5.02 |
| Sodium Lauryl Sulfate | 10.63 | 15.09 | 21.25 | 15.09 | 31.88 | 14.97 | 42.50 | 19.95 |
| Magnesium stearate | 1.26 | 1.78 | 2.51 | 1.78 | 3.80 | 1.78 | 3.80 | 1.78 |
| Aerosil 200 | 0.38 | 0.53 | 0.75 | 0.53 | 1.10 | 0.52 | 1.10 | 0.52 |
| Total | 70.40 | 100.00 | 140.80 | 100.00 | 213.00 | 100.00 | 213.00 | 100.00 |
| | 01B4 barrier | | | | | | | |
| Methocel E50 | 22.50 | 25.00 | 25.00 | 25.00 | 50.00 | 25.00 | 50.00 | 25.00 |
| HPMC Phthalate HP50 | 11.93 | 13.25 | 13.25 | 13.25 | 26.50 | 13.25 | 26.50 | 13.25 |
| Lactose pulvis H2O | 34.52 | 38.35 | 38.35 | 38.35 | 76.70 | 38.35 | 76.70 | 38.35 |
| Compritol 888 ATO | 16.56 | 18.40 | 18.40 | 18.40 | 36.80 | 18.40 | 36.80 | 18.40 |
| Plasdone K29-32 | 3.15 | 3.50 | 3.50 | 3.50 | 7.00 | 3.50 | 7.00 | 3.50 |
| Mg stearate | 0.90 | 1.00 | 1.00 | 1.00 | 2.00 | 1.00 | 2.00 | 1.00 |
| Aerosil 200 | 0.45 | 0.50 | 0.50 | 0.50 | 1.00 | 0.50 | 1.00 | 0.50 |
| Total | 90.00 | 100.00 | 100.00 | 100.00 | 200.00 | 100.00 | 200.00 | 100.00 |
| Total tablet weight, uncoated | 230.40 | | 340.80 | | 563.00 | | 563.00 | |

| | mg/tablet | % wt gain | mg/tablet | % wt gain | mg/tablet | % wt gain | mg/tablet | % wt gain |
|---|---|---|---|---|---|---|---|---|
| Opadry II Beige, 49B97383 | 11.52 | 5.00 | — | — | — | — | — | — |
| Opadry II Yellow, 49B92439 | — | — | 7.04 | 5.00 | — | — | — | — |
| Opadry II Beige, 49B97382 | — | — | — | — | 28.15 | 5.00 | — | — |
| Opadry II Beige, 49B97379 | — | — | — | — | — | — | 28.15 | 5.00 |
| Total tablet weight, coated | 241.92 | — | 347.84 | — | 591.15 | — | 591.15 | — |

TABLE 12-continued

| Nisoldipine Multilayer Tablet Formulations | | | | |
|---|---|---|---|---|
| | mg/tablet | mg/tablet | mg/tablet | mg/tablet |
| Opacode Black (S-1-27794) | 0.20 | 0.20 | 0.33 | 0.33 |
| Total tablet weight, coated, imprinted | 242.12 | 348.04 | 591.48 | 591.48 |

Example 5

Bioequivalence of Lower Dose SULAR GEOMATRIX (34 mg Nisoldipine) with SULAR (40 mg Nisoldipine)

The bioequivalence of 34 mg nisoldipine SULAR® GEOMATRIX® (i.e., GEOMATRIX) with 40 mg nisoldipine SULAR® was confirmed with a single-dose, open-label, randomized, four-period, two-treatment, two-sequence replicate design crossover study. The study compared the rate of absorption and oral bioavailability of a test formulation, GEOMATRIX® 16-E, 34 mg tablets (Treatment E) versus that of the reference product, SULAR® 40 mg tablets (Treatment F) following an overnight fast of at least 10 hours.

Study Design

This was a pivotal, single-dose, open-label, randomized, four-period, two-treatment, two-sequence replicate-design crossover study in which fifty-two (52) healthy adult subjects were scheduled to receive four separate single-dose administrations of nisoldipine extended-release tablets in four study periods following an overnight fast of at least 10 hours. Attempts were made to enroll an equal number of male and female subjects. Subjects who successfully completed the screening process checked into the research center the night before dosing. Subjects who continued to meet inclusion/exclusion criteria the morning of dose were assigned a subject number, based on the order in which they successfully completed the screening process and procedures as outlined in the study protocol. Dosing days were separated by a washout period of at least 7 days.

Subjects received each of the treatments listed below twice in a 2-sequence randomized fashion during the four treatment periods. Test product "Treatment E" is GEOMATRIX® 16-E nisoldipine extended-release tablet administered in one 34 mg tablet. Reference product "Treatment F" is SULAR® extended-release tablet administered in one 40 mg tablet.

Clinical Procedures Summary

During each study period, 6 mL blood samples were obtained prior to each dosing and following each dose at selected times through 36 hours post-dose. Two 6 mL blood samples were obtained at 48, 60, and 72 hours post-dose. A total of 96 PK blood samples were to be collected from each subject, 24 samples in each of four separate study periods.

In addition, blood was drawn and urine was collected for clinical laboratory testing (blood chemistries, hematology and urinalysis) at screening, baseline (Period 1 check-in), and at end-of-study discharge (72-hour procedures at Period 4). In addition, blood was drawn at check-in the evening before dosing in each of Periods 2, 3, and 4 for hematocrit and hemoglobin evaluations, which were reviewed by the Investigator prior to dosing in each of the three periods. Forty-nine (49) of the 52 subjects enrolled completed at least two periods of the study.

Procedures for Collecting Samples for Pharmacokinetic Analysis

Blood samples (1×6 mL, 2×6 mL) were collected in vacutainer tubes containing $K_2$-EDTA as a preservative at pre-dose (0) and at 1.0, 2.0, 3.0, 4.0, 5.0, 6.0, 7.5, 9.0, 10.5, 12.0, 14.0, 18.0, 24.0, 26.0, 28.0, 30.0, 36.0, 48.0, 60.0, and 72.0 hours after dosing during each study period.

Bioanalytical Summary

Plasma samples were analyzed for nisoldipine using validated LC-MS-MS procedures. The methods were validated for ranges of 0.0150 to 10.0 ng/mL and 1.00 to 100 pg/mL, based on the analysis of 0.250 mL and 1.00 mL of plasma, respectively.

Pharmacokinetic Analysis

Data from 49 subjects who successfully completed at least two study periods (one test, one reference) without protocol violation were included in the pharmacokinetic and statistical analyses. Three subjects did not complete the study; samples from these subjects were not analyzed. Two subjects experienced emesis during the study; these subjects were determined to be not evaluable for the period(s) in which emesis occurred during this comparative study of extended-release nisoldipine formulations. Although concentration-time data were acquired and retained in the data listing, data for one subject in Period 2 (Treatment E) and one subject in Period 4 (Treatment E) were excluded from the pharmacokinetic analysis set.

Concentration-time data were transferred from Watson LIMS directly to WinNonlin Enterprise Edition (Version 4.0, Pharsight Corporation) using the Custom Query Builder option for analysis. Data were analyzed by noncompartmental methods in WinNonlin. Concentration-time data that were below the limit of quantification (BLQ) were treated as zero in the data summarization and descriptive statistics. In the pharmacokinetic analysis, BLQ concentrations were treated as zero from time-zero up to the time at which the first quantifiable concentration was observed; embedded and/or terminal BLQ concentrations were treated as "missing." Full precision concentration data (not rounded to three significant figures) and actual sample times were used for all pharmacokinetic and statistical analyses.

The following pharmacokinetic parameters were calculated: peak concentration in plasma ($C_{max}$), time to peak concentration ($T_{max}$), elimination rate constant ($\lambda_z$), terminal half-life ($T_{1/2}$), area under the concentration-time curve from time-zero to the time of the last quantifiable concentration ($AUC_{last}$), and area under the plasma concentration time curve from time-zero extrapolated to infinity ($AUC_{inf}$).

Analysis of a linear mixed effect and the Schuirmann's two one-sided t-test procedures at the 5% significance level were applied to the log-transformed pharmacokinetic exposure parameters, $C_{max}$, $AUC_{last}$, and $AUC_{inf}$. The 90% confidence interval for the ratio of the geometric means (Test/Reference) was calculated. Bioequivalence was declared if the lower and upper confidence intervals of the log-transformed parameters were within 80% to 125%.

Results

Plasma concentration-time data and pharmacokinetic parameters were summarized by treatment. Since subjects were scheduled to receive each treatment on two occasions, descriptive statistics by treatment are based on 93 to 95 observations. Quantifiable pre-dose concentrations were observed for some subjects. However, since the pre-dose concentrations were well below 5% of $C_{max}$ for these subjects after a given treatment, the pre-dose concentrations were included in all pharmacokinetic analyses without adjustment.

The pharmacokinetic data and statistical analyses are shown below in Table 13 and Table 14. Due to the presence of secondary peaks and variability in the terminal phase of some individual profiles, lambda-z ($\lambda_z$) was estimated via linear regression of log concentration versus time data in WinNonlin. The data points that were included in the calculation were based on the regression with the largest adjusted $R^2$ value. This default estimation of $\lambda_z$ was used throughout this study for all pharmacokinetic analyses.

Conclusions

The 90% confidence interval for comparing the maximum exposure, based on $\ln(C_{max})$, is within the accepted 80% to 125% limits. The 90% confidence intervals for comparing total systemic exposure, based on $\ln(AUC_{last})$ and $\ln(AUC_{inf})$, are within the accepted 80% to 125% limits. Therefore, the test formulation of CGEOMATRIX® 16-E, 34 mg tablets is bioequivalent to the reference product, SULAR® 40 mg tablets, under fasting conditions.

Figure 2:
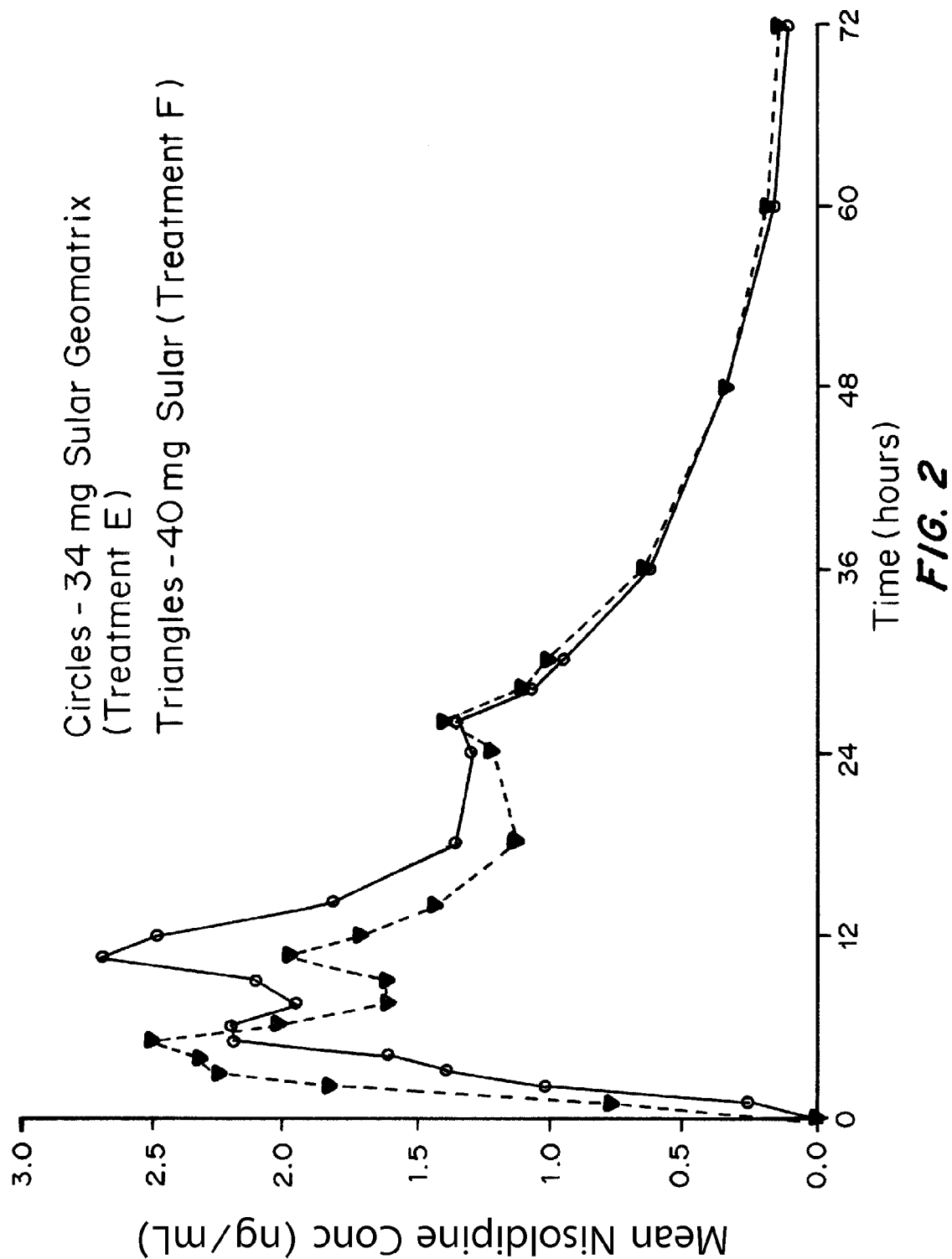
FIG. 2 is a graph of the mean nisoldipine concentration (ng/mL) versus time (in hours) for administration of the test formulation 16-E (34 mg nisoldipine SULAR GEOMATRIX, Treatment E) and the Reference Product (40 mg nisoldipine SULAR, Treatment F), under fasting conditions.

FIG. 2 shows the mean nisoldipine concentration time profiles after administration of test formulation 16-E (SULAR GEOMATRIX-Formulation E, 34 mg nisoldipine) and the referenced product (SULAR, Formulation F, 40 mg nisoldipine).

Example 6

Bioequivalence of Lower Dose SULAR GEOMATRIX (8.5 mg Nisoldipine) with SULAR (10 mg Nisoldipine)

The bioequivalence of 8.5 mg nisoldipine SULAR® GEOMATRIX® with 10 mg nisoldipine SULAR® was confirmed with a single-dose, open label, randomized, four period, two-treatment, two-sequence replicate design crossover study. The study compared the rate of absorption and oral bioavailability of a test formulation, GEOMATRIX®16-E, 8.5 mg nisoldipine tablets (Treatment G) versus that of the reference product, SULAR® 10 mg nisoldipine tablets (Treatment H) following an overnight fast of at least 10 hours.

This was a pivotal, single-dose, open-label, randomized, four-period, two-treatment, two-sequence replicate-design crossover study in which fifty-two (52) healthy adult subjects were scheduled to receive four separate single-dose administrations of nisoldipine extended-release tablets in four study periods following an overnight fast of at least 10 hours.

TABLE 13

Pharmacokinetic Parameters of Nisoldipine after Administration of Test Formulation 16-E (GEOMATRIX, Treatment E) and the Reference Product (SULAR, Treatment F)

| Parameter | Treatment E: Test Formulation 16-E (GEOMATRIX) | | | | Treatment F: Reference Product (SULAR) | | | |
|---|---|---|---|---|---|---|---|---|
| | n | Mean | SD | CV % | n | Mean | SD | CV % |
| $T_{max}$ (hr) | 93 | 9.22 | 5.13 | 55.61 | 95 | 8.49 | 7.79 | 91.84 |
| $C_{max}$ (ng/mL) | 93 | 3.79 | 3.56 | 93.97 | 95 | 3.58 | 3.05 | 85.08 |
| $AUC_{last}$ (hr*ng/mL) | 93 | 62.35 | 69.30 | 111.15 | 95 | 60.10 | 31.52 | 52.45 |
| $AUC_{inf}$ (hr*ng/mL) | 93 | 65.24 | 74.67 | 114.46 | 95 | 65.45 | 36.41 | 55.63 |
| $AUC_{Extrap}$ (%) | 93 | 3.84 | 3.41 | 88.68 | 95 | 6.43 | 8.77 | 136.33 |
| $\lambda_z$ (hr$^{-1}$) | 93 | 0.0554 | 0.0163 | 29.38 | 95 | 0.0527 | 0.0205 | 38.91 |
| $T_{1/2}$ (hr) | 93 | 13.68 | 4.25 | 31.05 | 95 | 17.08 | 13.74 | 80.49 |
| $T_{last}$ (hr) | 93 | 72.00 | 0.00 | 0.00 | 95 | 72.00 | 0.01 | 0.01 |
| $C_{last}$ (ng/mL) | 93 | 0.126 | 0.239 | 190.21 | 95 | 0.148 | 0.166 | 111.91 |

Note:
Full precision data used in pharmacokinetic analysis

TABLE 14

Statistical Analysis of the Log-Transformed Systemic Exposure Parameters of Nisoldipine Comparing Test Formulation 16-E (GEOMATRIX, Treatment E) to the Reference Product (SULAR, Treatment F)

| Dependent Variable | Geometric Mean[a] | | Ratio (%)[b] | 90% CI[c] | | Power |
|---|---|---|---|---|---|---|
| | Test | Ref | (Test/Ref) | Lower | Upper | |
| $\ln(C_{max})$ | 3.0723 | 2.9941 | 102.61 | 93.61 | 112.47 | 0.9899 |
| $\ln(AUC_{last})$ | 50.7356 | 54.6492 | 92.84 | 87.77 | 98.20 | 1.0000 |
| $\ln(AUC_{inf})$ | 52.7416 | 58.7395 | 89.79 | 84.37 | 95.56 | 1.0000 |

[a]Geometric Mean for the Test Formulation (Test) and Reference Product (Ref) based on Least Squares Mean of log-transformed parameter values
[b]Ratio(%) = Geometric Mean (Test)/Geometric Mean (Ref)
[c]90% Confidence Interval Attempts were made to enroll an equal number of male and female subjects. Subjects who continued to meet inclusion/exclusion criteria the morning of dose were assigned a subject number, based on the order in which they successfully completed the screening process and procedures as outlined in the study protocol. Dosing days were separated by a washout period of at least 7 days.

Subjects received each of the treatments listed below twice in a 2-sequence randomized fashion during the four treatment periods. Test product "Treatment G" is GEOMATRIX® nisoldipine extended-release tablet administered in one 8.5 mg tablet. Reference product "Treatment H" is SULAR® extended-release tablet administered in one 10 mg tablet.

Clinical Procedures Summary

During each study period, one 6 mL blood sample was obtained within 60 minutes prior to each dose administration and following each dose at selected times through 36 hours post-dose. Two 6 mL blood samples were obtained at 48, 60, and 72 hours post-dose. A total of 96 PK blood samples were to be collected from each subject, 24 samples in each of four separate study periods. Forty-Nine (49) of the 52 subjects enrolled completed at least two periods of the study.

Procedures for Collecting Samples for Pharmacokinetic Analysis

Blood samples (1×6 mL, 2×6 mL) were collected in vacutainer tubes containing $K_2$-EDTA as a preservative at predose (0) and at 1.0, 2.0, 3.0, 4.0, 5.0, 6.0, 7.5, 9.0, 10.5, 12.0, 14.0, 18.0, 24.0, 26.0, 28.0, 30.0, 36.0, 48.0, 60.0, and 72.0 hours after dosing during each study period.

Bioanalytical Summary

Plasma samples were analyzed for nisoldipine by CEDRA Corporation using validated LC-MS-MS procedures. The methods were validated for ranges of 0.0150 to 10.0 ng/mL and 1.00 to 100 pg/mL, based on the analysis of 0.250 mL and 1100 mL of plasma, respectively.

Pharmacokinetic Analysis

Data from 49 subjects who successfully completed at least the first two or at least the last two periods of the study (one test, one reference) without protocol violation were included in the pharmacokinetic and statistical analyses. Subject 501 experienced emesis in one study period. Although concentration-time data were acquired and retained in the data listing, this subject was determined to be not evaluable for all study periods and was excluded from the pharmacokinetic data set for the period(s) in which emesis occurred.

Concentration-time data were transferred from Watson LIMS directly to WinNonlin Enterprise Edition (Version 4.0, Pharsight Corporation) using the Custom Query Builder option for analysis. Data were analyzed by noncompartmental methods in WinNonlin. Concentration-time data that were below the limit of quantification (BLQ) were treated as zero in the data summarization and descriptive statistics. In the pharmacokinetic analysis, BLQ concentrations were treated as zero from time-zero up to the time at which the first quantifiable concentration was observed; embedded and/or terminal BLQ concentrations were treated as "missing." Full precision concentration data (not rounded to three significant figures) and actual sample times were used for all pharmacokinetic and statistical analyses.

The following pharmacokinetic parameters were calculated: peak concentration in plasma ($C_{max}$), time to peak concentration ($T_{max}$), elimination rate constant ($\lambda_z$) terminal half-life ($T_{1/2}$), area under the concentration-time curve from time-zero to the time of the last quantifiable concentration ($AUC_{last}$), and area under the plasma concentration time curve from time-zero extrapolated to infinity ($AUC_{inf}$).

Linear mixed-effects model procedures and the Schuirmann's two one-sided t-test procedures at the 5% significance level were applied to the log-transformed pharmacokinetic exposure parameters, $C_{max}$, $AUC_{last}$, and $AUC_{inf}$. The 90% confidence interval for the ratio of the geometric means (Test/Reference) was calculated. Bioequivalence was declared if the lower and upper confidence intervals of the log-transformed parameters were within 80% to 125%.

Results

Figure 3:
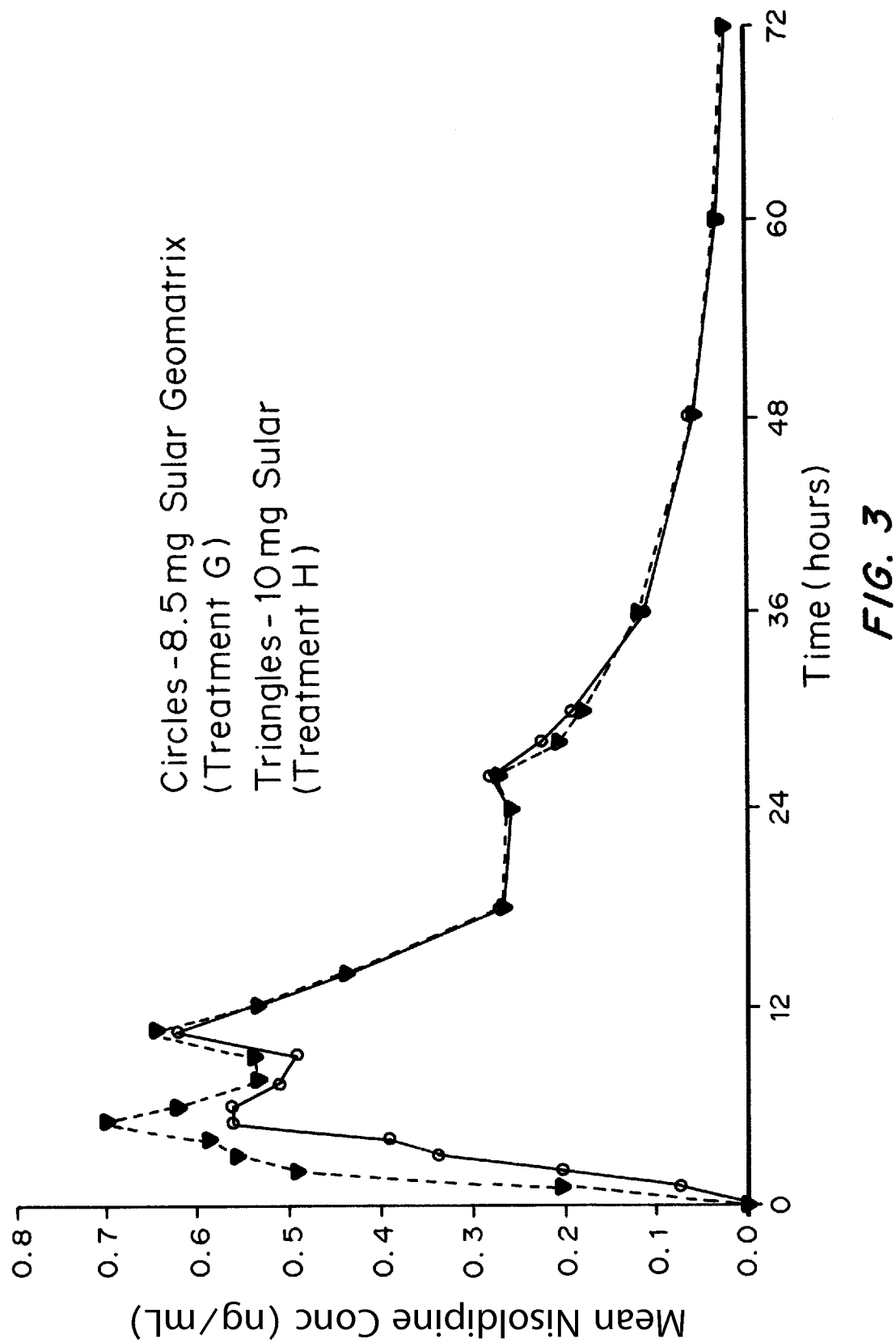
FIG. 3 is a graph of the mean nisoldipine concentration (ng/mL) versus time (in hours) for administration of the test formulation (8.5 mg nisoldipine SULAR GEOMATRIX, Treatment G) and the Reference Product (10 mg nisoldipine SULAR, Treatment H).

Plasma concentration-time data and pharmacokinetic parameters were summarized by treatment. Since subjects were scheduled to receive each treatment on two occasions, descriptive statistics by treatment are based on 96 or 94 observations. Mean concentration-time data are shown in FIG. 3. Results of the pharmacokinetic and statistical analyses are shown below in Table 15 and Table 16.

Conclusions

The 90% confidence interval for comparing the maximum exposure, based on $\ln(C_{max})$, is within the accepted 80% to 125% limits. The 90% confidence intervals for comparing total systemic exposure, based on $\ln(AUC_{last})$ and $\ln(AUC_{inf})$, are within the accepted 80% to 125% limits. Therefore, the test formulation, GEOMATRIX 8.5 mg tablets, is bioequivalent to the reference product, SULAR extended-release 10 mg tablets, under fasting conditions.

TABLE 15

Pharmacokinetic Parameters of Nisoldipine after Administration of Test Formulation 16-E (GEOMATRIX, Treatment G) and the Reference Product (SULAR, Treatment H)

| Parameter | Treatment G: Test Formulation 2B (GEOMATRIX) | | | | Treatment H: Reference Product (SULAR) | | | |
|---|---|---|---|---|---|---|---|---|
| | n | Mean | SD | CV % | n | Mean | SD | CV % |
| $T_{max}$ (hr) | 96 | 8.59 | 4.07 | 47.39 | 94 | 7.35 | 4.12 | 56.04 |
| $C_{max}$ (ng/mL) | 96 | 0.858 | 0.844 | 98.42 | 94 | 0.971 | 0.854 | 87.92 |
| $AUC_{last}$ (hr*ng/mL) | 96 | 13.29 | 9.135 | 68.74 | 94 | 14.54 | 9.864 | 67.81 |
| $AUC_{inf}$ (hr*ng/mL) | 96 | 13.80 | 9.435 | 68.37 | 94 | 15.28 | 10.43 | 68.25 |
| $AUC_{Extrap}$ (%) | 96 | 3.77 | 3.31 | 87.74 | 94 | 4.46 | 5.69 | 127.74 |
| $\lambda_z$ (hr$^{-1}$) | 96 | 0.0530 | 0.0162 | 30.60 | 94 | 0.0494 | 0.0171 | 34.68 |
| $T_{1/2}$ (hr) | 96 | 14.46 | 4.89 | 33.85 | 94 | 16.53 | 8.54 | 51.67 |
| $T_{last}$ (hr) | 96 | 72.00 | 0.00 | 0.00 | 94 | 72.00 | 0.01 | 0.01 |
| $C_{last}$ (ng/mL) | 96 | 0.0223 | 0.0209 | 93.78 | 94 | 0.0247 | 0.0246 | 99.66 |

TABLE 16

Statistical Analysis of the Log-Transformed Systemic Exposure Parameters of Nisoldipine Comparing Test Formulation 16-E (GEOMATRIX, Treatment G) to the Reference Product (SULAR, Treatment H)

| Dependent Variable | Geometric Mean[a] | | Ratio (%)[b] (Test/Ref) | 90% CI[c] | | Power |
|---|---|---|---|---|---|---|
| | Test | Ref | | Lower | Upper | |
| $\ln(C_{max})$ | 0.7013 | 0.7942 | 88.30 | 81.68 | 95.46 | 0.9985 |
| $\ln(AUC_{last})$ | 11.5097 | 12.5263 | 91.88 | 86.66 | 97.42 | 1.0000 |
| $\ln(AUC_{inf})$ | 11.9760 | 13.1365 | 91.17 | 85.93 | 96.72 | 1.0000 |

We claim:

1. A controlled release solid oral dosage formulation comprising
   (a) a central core layer comprising about 8 mg to about 34 mg of the calcium channel blocker nisoldipine or a derivative, analogue, or polymorph thereof and pharmaceutically acceptable salts thereof, and one or more enteric materials, wherein the calcium channel blocker is not coated with the one or more enteric materials; and
   (b) one or more barrier layers above or below the central core layer comprising one or more swellable, erodible, or gellable polymers,
   wherein the formulation is bioequivalent to a second formulation comprising an amount of nisoldipine that is about 16% more and which comprises only an enteric polymer coating on the core or central layer.

2. The formulation of claim 1, wherein the one or more enteric materials is selected from the group consisting of cellulose acetate phthalate, alginates, alkali-soluble acrylic resins, hydroxypropyl methylcellulose phthalate, methacrylate-methacrylic acid co-polymers, polyvinyl acetate phthalate, styrol maleic acid copolymers, and combinations thereof, wherein the concentration of the one or more enteric materials is from about 0.1% to about 20% by weight of the core.

3. The formulation of claim 1, wherein the central core layer further comprises one or more materials that modulate the release of the calcium channel blocker selected from the group consisting of crosslinked polyvinylpyrrolidone, hydroxypropylmethylcellulose, hydroxypropylcellulose, crosslinked sodium carboxymethylcellulose, carboxymethyl starch, acrylic and methacrylic acid polymers and copolymers, polyesters, polyanhydrides, polymethylvinylether/anhydride copolymers, potassium methacrylate-divinylbenzene copolymer, polyvinylalcohols, glucan, scleroglucan, mannan, starch and derivatives thereof, betacyclodextrins, other cyclodextrins derivatives, glyceryl monostearate, triglyceride derivatives, semi-synthetic glycerides, hydrogenated castor oil, glyceryl palmitostearate, cetyl alcohol, polyvinylpyrrolidone, glycerol, ethylcellulose, methylcellulose, sodium carboxymethylcellulose, magnesium stearate, stearic acid, talc, sodium benzoate, boric acid, polyoxyethyleneglycols, colloidal silica, and combinations thereof, wherein the one or more materials that modulate the release of the calcium channel blocker are present in a concentration from about 1% to about 90% by weight of the core.

4. The formulation of claim 1, wherein the one or more swellable, erodible, or gellable polymers are selected from the group consisting of hydroxypropylmethylcellulose, carboxyvinyl polymers; polyvinylalcohols; glucans, scleroglucans; mannans; xanthans; alginates and derivatives thereof; polyanhydrides; polyaminoacids; methylvinylether/maleic anhydride copolymers; carboxymethylcellulose and derivatives thereof, ethylcellulose, methylcellulose, and other celluloses; and combinations thereof, wherein the concentration of the one or more swellable, erodible, or gellable polymers is from about 5% to about 90% by weight of the barrier layer(s).

5. The formulation of claim 4, wherein the polymer is hydroxypropyl methyl-cellulose.

6. The formulation of claim 1, further comprising one or more coating materials that modulate release of the calcium channel blocker selected from the group consisting of immediate release coatings, taste masking coatings, sustained released coatings, enteric coatings in combination with another coating that modulates release, delayed release coatings, and combinations thereof.

7. The formulation of claim 1, wherein the core comprises from about 15 weight percent to about 45 weight percent of a hydroxymethyl propylcellulose compound, and from about 10 weight percent to about 20 weight percent of a metal alkyl sulfate; and wherein at least one barrier layer comprises from about 10 weight percent to about 50 weight percent of a hydroxymethyl propylcellulose.

8. The formulation of claim 7, wherein the hydroxymethyl propylcellulose comprises hydroxypropyl methylcellulose type 2208.

9. The formulation of claim 1, wherein the $T_{max}$ of the calcium channel blocker is from about 3.85 hours to about 15 hours.

10. The formulation of claim 1, wherein the $AUC_{inf}$ of the calcium channel blocker is from about 41.8 hr*ng/ml to about 103.8 hr*ng/ml.

11. The formulation of claim 1 in a dosage form providing a $C_{max}$ of the calcium channel blocker from about 0.23 ng/ml to about 7.35 ng/ml under fasted conditions based on a 34 mg dose.

12. The formulation of claim 1, wherein the $T_{max}$ of the calcium channel blocker is from about 4 hours to about 14.5 hours.

13. The formulation of claim 1, wherein the $AUC_{inf}$ of the calcium channel blocker is from about from about 28 hr*ng/ml to about 102 hr*ng/ml.

14. The formulation of claim 1 in a dosage form providing a $C_{max}$ of the calcium channel blocker from about 0.17 ng/ml to about 5.5 ng/ml under fasted conditions based on a 25.5 mg dose.

15. The formulation of claim 1, wherein the $AUC_{inf}$ of the calcium channel blocker is from about 21 hr*ng/ml to about 76.5 hr*ng/ml.

16. The formulation of claim 1 in a dosage form providing a $C_{max}$ of the calcium channel blocker from about 0.11 ng/ml to about 3.66 ng/ml under fasted conditions based on a 17 mg dose.

17. The formulation of claim 1, wherein the $AUC_{inf}$ of the calcium channel blocker from about 14 hr*ng/ml to about 51 hr*ng/ml.

18. The formulation of claim 1 in a dosage form providing a $C_{max}$ of the calcium channel blocker from about 0.014 ng/ml to about 1.7 ng/ml under fasted conditions based on a 8.5 mg dose.

19. The formulation of claim 1, wherein the $T_{max}$ of the calcium channel blocker is from about 4.5 hours to about 12.7 hours.

20. The formulation of claim 1, wherein the $AUC_{inf}$ of the calcium channel blocker is from about 4.3 hr*ng/ml to about 23.25 hr*ng/ml.

21. The formulation of claim 1 in a dosage form providing a $C_{max}$ from about 5 ng/ml to about 13 ng/ml under fed conditions.

22. The formulation of claim 1, wherein the dosage form provides a $T_{max}$ of from about 3.7 hours to about 8.6 hours.

23. The formulation of claim 1, wherein the dosage form provides an $AUC_{inf}$ from about 31 hr*ng/ml to about 66 hr*ng/ml.

24. The formulation of claim 1, wherein the amount of nisoldipine in the formulation is selected from the group consisting of 8.5 mg, 17 mg, 25.5 mg, and 34 mg, and the amount of nisoldipine in the second formulation is selected from the group consisting of 10 mg, 20 mg, 30 mg, and 40 mg.

* * * * *